US009408997B2

(12) United States Patent
Kelley

(10) Patent No.: US 9,408,997 B2
(45) Date of Patent: Aug. 9, 2016

(54) SYSTEM AND METHOD FOR THE TREATMENT OF INSOMNIA

(71) Applicant: InSomniSolv, Inc., Hampton Falls, NH (US)

(72) Inventor: Peter Kelley, Hampton Falls, NH (US)

(73) Assignee: Insomnisolv, Inc., Hampton Falls, NH (US)

( * ) Notice: Subject to any disclaimer, the term of this patent is extended or adjusted under 35 U.S.C. 154(b) by 188 days.

(21) Appl. No.: 14/189,747

(22) Filed: Feb. 25, 2014

(65) Prior Publication Data

US 2014/0179986 A1    Jun. 26, 2014

Related U.S. Application Data

(63) Continuation-in-part of application No. PCT/US2012/052234, filed on Aug. 24, 2012.

(60) Provisional application No. 61/527,205, filed on Aug. 25, 2011.

(51) Int. Cl.
*A61M 21/02* (2006.01)
*A61B 5/00* (2006.01)
(Continued)

(52) U.S. Cl.
CPC ............... *A61M 21/02* (2013.01); *A61B 5/4806* (2013.01); *A61N 1/36025* (2013.01);
(Continued)

(58) Field of Classification Search
CPC .............. A61B 5/4806; A61N 1/0456; A61M 2230/63; A61M 2230/50; A61M 2230/42; A61M 2230/10; A61M 2230/06; A61M 2205/52; A61M 2205/505; A61M 2205/3592; A61M 2205/3569; A61M 21/02; A61M 1/36025; A61M 1/36135; A61M 2021/0022; A61M 2021/0027; A61M 2021/0044; A61M 2021/0072; A61M 2205/332; A61M 2230/005
See application file for complete search history.

(56) References Cited

U.S. PATENT DOCUMENTS

| | | | | |
|---|---|---|---|---|
| 6,488,617 B1 * | 12/2002 | Katz | ..................... | A61B 5/0482 600/26 |
| 2006/0161218 A1 * | 7/2006 | Danilov | ............... | A61B 5/0492 607/45 |

(Continued)

FOREIGN PATENT DOCUMENTS

EP          1618913 A1     1/2006

OTHER PUBLICATIONS

Supplementary European Search Report issued Feb. 24, 2015 corresponding to European Application No. 12825131.1 (6 sheets).

*Primary Examiner* — Christine H Matthews
*Assistant Examiner* — Joshua D Lannu
(74) *Attorney, Agent, or Firm* — Tom Engellenner; Reza Mollaaghababa; Pepper Hamilton, LLP.

(57) ABSTRACT

A system and method that provides controlled bilateral stimulation to a patient in response to physiological feedback to initiate and/or accelerate the onset of sleep and to maintain the sleep state after the onset of sleep. The system induces bilateral stimulation through stimulation modules that are coupled to opposite lateral sides of the patient's body. The stimulation modules stimulate the patient's body bilaterally through a sequence of stimulations that alternate from one side of the patient's body to the other with a pause between each successive stimulation. The system controls the duration of the stimulations, the intensity of the stimulations and the period of time between successive stimulations in response to feedback from physiological sensors. The sensors are coupled to the patient and provide physiological information which initiates or terminates the bilateral stimulations, and/or modifies the characteristics of the stimulations.

42 Claims, 9 Drawing Sheets

(51) Int. Cl.
 *A61N 1/36* (2006.01)
 *A61N 1/04* (2006.01)
 *A61M 21/00* (2006.01)

(52) U.S. Cl.
 CPC .......... *A61M 2021/0022* (2013.01); *A61M 2021/0027* (2013.01); *A61M 2021/0044* (2013.01); *A61M 2021/0072* (2013.01); *A61M 2205/332* (2013.01); *A61M 2205/3569* (2013.01); *A61M 2205/3592* (2013.01); *A61M 2205/505* (2013.01); *A61M 2205/52* (2013.01); *A61M 2230/06* (2013.01); *A61M 2230/10* (2013.01); *A61M 2230/42* (2013.01); *A61M 2230/50* (2013.01); *A61M 2230/63* (2013.01); *A61N 1/0456* (2013.01); *A61N 1/36135* (2013.01)

(56) References Cited

U.S. PATENT DOCUMENTS

| | | | |
|---|---|---|---|
| 2008/0051852 A1* | 2/2008 | Dietrich | A61H 39/002 607/45 |
| 2008/0208287 A1 | 8/2008 | Palermo et al. | |
| 2008/0249439 A1* | 10/2008 | Tracey | A61H 39/04 601/46 |
| 2008/0269652 A1* | 10/2008 | Reiner | 601/15 |
| 2008/0288023 A1* | 11/2008 | John | A61N 1/37247 607/59 |
| 2009/0192556 A1 | 7/2009 | Wu et al. | |
| 2009/0203972 A1* | 8/2009 | Heneghan | A61B 5/0507 600/301 |
| 2010/0145410 A1 | 6/2010 | Kirsch et al. | |
| 2011/0201977 A1 | 8/2011 | Tass | |

\* cited by examiner

SYSTEM AND METHOD FOR THE TREATMENT OF INSOMNIA

CROSS REFERENCE TO RELATED APPLICATIONS

This application claims priority as a continuation-in-part to PCT Application No. PCT/US12/52234, entitled "System and Method for The Treatment of Insomnia" filed on Aug. 24, 2012, which claims priority to U.S. Provisional Application No. 61/527,205 entitled "System and Method for The Treatment of Insomnia" filed on Aug. 25, 2011, the entire contents of which are hereby incorporated by reference in their entireties.

TECHNICAL FIELD

The present invention relates to devices and methods used in the treatment of insomnia, and more particularly to devices and methods that initiate and/or accelerate the onset of sleep and devices and methods that maintain sleep after onset of sleep, in response to physiological feedback.

The present invention provides a novel, non-invasive medical device for treating insomnia, by initiating and maintaining sleep employing bilateral stimulation in conjunction with physiological feedback.

BACKGROUND

Prior treatments for insomnia are primarily limited to behavioral therapy, including Cognitive Behavioral Therapy for Insomnia (CBT-I) and to pharmacological therapy including over the counter medications. Behavioral therapies are lengthy processes, which depend upon the patient's ability to maintain compliance with specific therapeutic activities. Pharmacological therapies raise concerns over long-term use, physiological side effects, and addictive responses.

In general, insomnia presents in multiple manifestations, including latency of sleep onset and waking after sleep onset. Furthermore, insomnia may present as a primary condition or as a secondary condition to other morbidities, including depression, anxiety and post-traumatic stress disorder.

The current practice for diagnosing sleep disorders includes administering a Polysomnogram (PSG), which measures biophysiological activity during sleep. The PSG employs Electroencephalography (EEG) to measure electrical activity within the brain. The EEG data are used to determine the wakefulness of the patient.

Current practice for diagnosing sleep disorders also includes actigraphy, which uses actimetry sensors composed of accelerometers to measure gross motor activity to determine the wakefulness of the patient.

A type of psychotherapy used in the treatment of trauma known as Eye Movement Desensitization and Reprocessing, EMDR, uses bilateral stimulation in conjunction with other psychotherapy mechanisms to achieve more rapid recovery from traumatic events than is normally achieved without bilateral stimulation. It is believed that the bilateral stimulation produces shifts in regional brain activation and neuromodulation similar to those produced during REM sleep, and that this activation shifts the brain into a memory-processing mode similar to that of REM sleep, which permits the integration of traumatic memories.

There are numerous approaches that have been employed to treat and/or ameliorate the effects of insomnia and the ability to maintain a started sleep. One such approach is common behavioral therapy for treating insomnia including stimulus control, such as not working, reading or watching TV in bed, which attempts to eliminate the association of the bed with negative outcomes such as wakefulness and to create a positive association between the bed and sleep.

Another common behavioral therapy for treating insomnia is relaxation training where activities such as guided imagery and muscle relaxation are used to reduce arousal states, which interfere with sleep.

Another common behavioral therapy for treating insomnia is sleep restriction, which limits the amount of time spent in bed when not asleep, and prohibits sleeping during non-prescribed times, e.g. afternoon napping, in order to improve the continuity of sleep.

Another common behavioral therapy for treating insomnia is Cognitive Behavior Therapy for Insomnia (CBT-I), which combines cognitive behavior therapy with other behavior therapies such as sleep restriction, stimulus control and relaxation training.

Another common behavioral therapy for treating insomnia is sleep hygiene, which teaches patients about practices that improve sleep, such as proper diet, exercise, avoiding stimulants, maintaining a quiet sleep environment and avoiding napping.

Another common behavioral therapy for treating insomnia is biofeedback therapy, which utilizes auditory or visual feedback to control some physiological variable in order to reduce arousal states, which interfere with sleep.

Some patients with insomnia are treated with multicomponent behavioral therapy, which combines two or more of the common behavioral therapies.

A common pharmacological therapy for treating insomnia is use of Benzodiazepine Receptor Agonistic Modulators (BzRAs), which act as a hypnotic to induce and maintain sleep.

Another common pharmacological therapy for treating insomnia is use of Non Benzodiazepine Receptor Agonistic Modulators (Non BzRAs), which act as a hypnotic to induce and maintain sleep.

Another common pharmacological therapy for treating insomnia is use of melatonin receptor agonists, which are used primarily for inducing sleep.

Another common pharmacological therapy for treating insomnia is use of a low dose sedating antidepressant, which may be used with comorbid depression.

Some pharmacological therapies for treating insomnia include combinations of BzRAs or Non BZRAs and antidepressants.

Some patients with insomnia treat themselves with over-the-counter antihistamines.

Some patients with insomnia treat themselves with over-the-counter antihistamine-analgesic combinations.

Some patients with insomnia treat themselves with over-the-counter vale an extracts.

Some patients with insomnia treat themselves with over-the-counter melatonin.

Another experimental treatment for treating insomnia is cranial electrotherapy stimulation, which induces a pulsed electric current through the brain using electrodes attached to the scalp or earlobes.

All of the forgoing approaches have disadvantages, which limit their effectiveness. Pharmacological treatments have complications including addiction, amnesia, hallucinations, depression, confusion, suicide ideation and daytime sleepiness. Behavioral therapy techniques are expensive and time consuming, and patients have difficulty complying with protocols. Cranial electrotherapy stimulation is used during daytime and is not an active therapeutic for inducing or maintaining sleep.

A new treatment is needed that is applied in response to a patient's individual physiology, which will actively assist the patient in achieving and maintaining sleep, and which does not have undesirable side effects.

SUMMARY OF THE INVENTION

In accordance with the present invention, providing bilateral stimulation to a patient, independent of the other psychotherapeutic mechanisms together with EMDR, is believed to produce shifts in regional brain activation and neuromodulation similar to those produced during REM sleep thus accelerating the onset of sleep. By analyzing certain physiological data such as EEG, actigraph or other physiological data it is possible to determine when a patient is aroused from sleep and, under such condition applying bilateral stimulation to the patient which produces shifts in regional brain activation and neuromodulation similar to those produced during REM sleep thus maintaining the patient's sleep state.

More specifically, the present invention provides a medical device, which initiates and/or accelerates the onset of sleep, and maintains the sleep state after sleep onset. The device controls delivery of bilateral stimulation to the patient in response to physiological signals received from the patient. In one embodiment the device includes one or more patient worn modules, which communicate with a controller.

The patient worn modules typically comprise (a) one or more stimulators; (b) one or more physiological sensors; (c) one or more communication mechanisms; (d) memory; and (e) a processor, which is coupled to the stimulators, sensors, communication mechanisms and memory. The sensors are typically coupled to the patient and are designed to detect physiological signals, which may originate from brain wave activity, body movement, respiration, heart rate, body temperature, blood pressure or other physiological sources, or combinations thereof. The stimulators are coupled to the patient and produce a physiological stimulation. The stimulation may comprise tactile, auditory, visual, neurological or other physiological stimulation, or combinations thereof.

The controller typically comprises (a) a touch sensitive screen; (b) one or more communication mechanisms; (c) memory; and (d) a processor, which is coupled to the screen, communication mechanisms and memory.

The controller transmits signals either directly or wirelessly via the communication mechanisms to the patient worn modules, which control the behavior of the stimulators to create a repeating pattern of stimulation in response to feedback from the physiological sensors. The pattern of stimulation is such that a first stimulator is activated for a period of time, followed by a period of time when no stimulator is activated, followed by activation of a second stimulator for a period of time (typically on the opposite lateral side of the patient's body, sometimes hereinafter referred to as "alternate bilateral stimulation" or ABS), followed by a period of time when no stimulator is activated.

The controller incorporates user accessible controls, which can be used manually to modify the parameters of the signals that are transmitted to the patient worn modules. Alternatively, the controller may be configured to automatically modify the signals that are transmitted to the patient worn modules in direct response to physiological feedback. These parameters determine the characteristics of the repeating pattern of stimulation and may include the duration of time during which the stimulators are activated, the duration of time between successive stimulator activations, the relative intensity of the stimulations, and the initiation and cessation of the repeating pattern of stimulation.

The sensors are coupled to the patient in such a manner as to be able to detect physiological signals from the patient. The processor in the patient worn module processes these signals and generates physiological data, which may be periodically transmitted to the controller via the communication mechanisms.

The processor in the patient worn module is optionally programmed to use the physiological data to determine one or more characteristics of the state of wakefulness of the patient, which may be periodically transmitted to the controller via the communication mechanisms. The processor in the patient worn module is also optionally programmed to automatically alter the characteristics of the repeating pattern of stimulation in response to one or more characteristics of the state of wakefulness of the patient.

The processor in the controller is optionally programmed to use the physiological data transmitted from the patient worn module to determine one or more characteristics of the state of wakefulness of the patient. The processor is also programmed to automatically alter the characteristics of the repeating pattern of stimulation in response to one or more characteristics of the state of wakefulness of the patient.

The processor in the controller is also programmed to automatically alter the characteristics of the repeating pattern of stimulation in response to one or more characteristics of the state of wakefulness of the patient transmitted from the patient worn module.

BRIEF DESCRIPTION OF DRAWINGS

The invention will be more fully understood by referring to the following Detailed Description of Specific Embodiments in conjunction with the Drawings, of which.

DETAILED DESCRIPTION

Definitions

Insomnia is characterized by a complaint of difficulty initiating sleep, maintaining sleep, and/or nonrestorative sleep that causes clinically significant distress or impairment in social, occupational, or other important areas of functioning.

Cognitive behavior therapy is a form of psychotherapy that emphasizes the role of thinking in how we feel and what we do. It is based on the idea that our thoughts cause our feelings and behaviors, not external things, like people, situations, and events.

Polysomnogram (PSG) is the test result from a Polysomnography study, which is a multi-parametric test used in the study of sleep and as a diagnostic tool in sleep medicine.

Electroencephalography (EEG) is the recording of electrical activity of the brain. EEG measures voltage fluctuations resulting from ionic current flows within the neurons of the brain. EEG is one of the parameters employed in a PSG.

EEG sensors are electrodes used to measure the electrical activity of the brain during EEG.

Bilateral stimulation is an activity that alternately stimulates opposite hemispheres of the brain. It may be accomplished in multiple ways including applying audio, tactile or visual stimulation alternately to opposite lateral sides of the body.

Eye movement desensitization and reprocessing (EMDR) is a form of psychotherapy used to resolve the development of trauma-related disorders caused by exposure to distressing events such as rape or military combat. EMDR uses a structured eight-phase approach and incorporates bilateral stimulation during one or two of the phases.

A vibration motor is a type of electrical motor used in hand-held devices to provide tactile feedback to the user in the form of vibrations. It may be constructed with an eccentric mass counter weight mounted to the shaft of a small circular motor, or a mass mounted to the shaft of a small linear motor. These are commonly used in consumer devices such as cell phones.

An accelerometer is an electromechanical device that measures acceleration forces.

An actimetry sensor is a patient worn device, which uses accelerometers to measure gross motor activity.

Actigraphy is a widely accepted technology, which uses actimetry sensors to determine sleep/wake patterns for the diagnosis and monitoring of sleep disorders such as insomnia.

An electroactive polymer is a type of material that contracts and expands when stimulated with an electrical current.

A communication mechanism is a means for two or more electronic devices to exchange information. This may take multiple forms including standard computer interfaces, e.g. USB and LAN, as well as wireless mechanisms including Blue Tooth and Zigbee.

FIG. 1 Description

Figure 1:
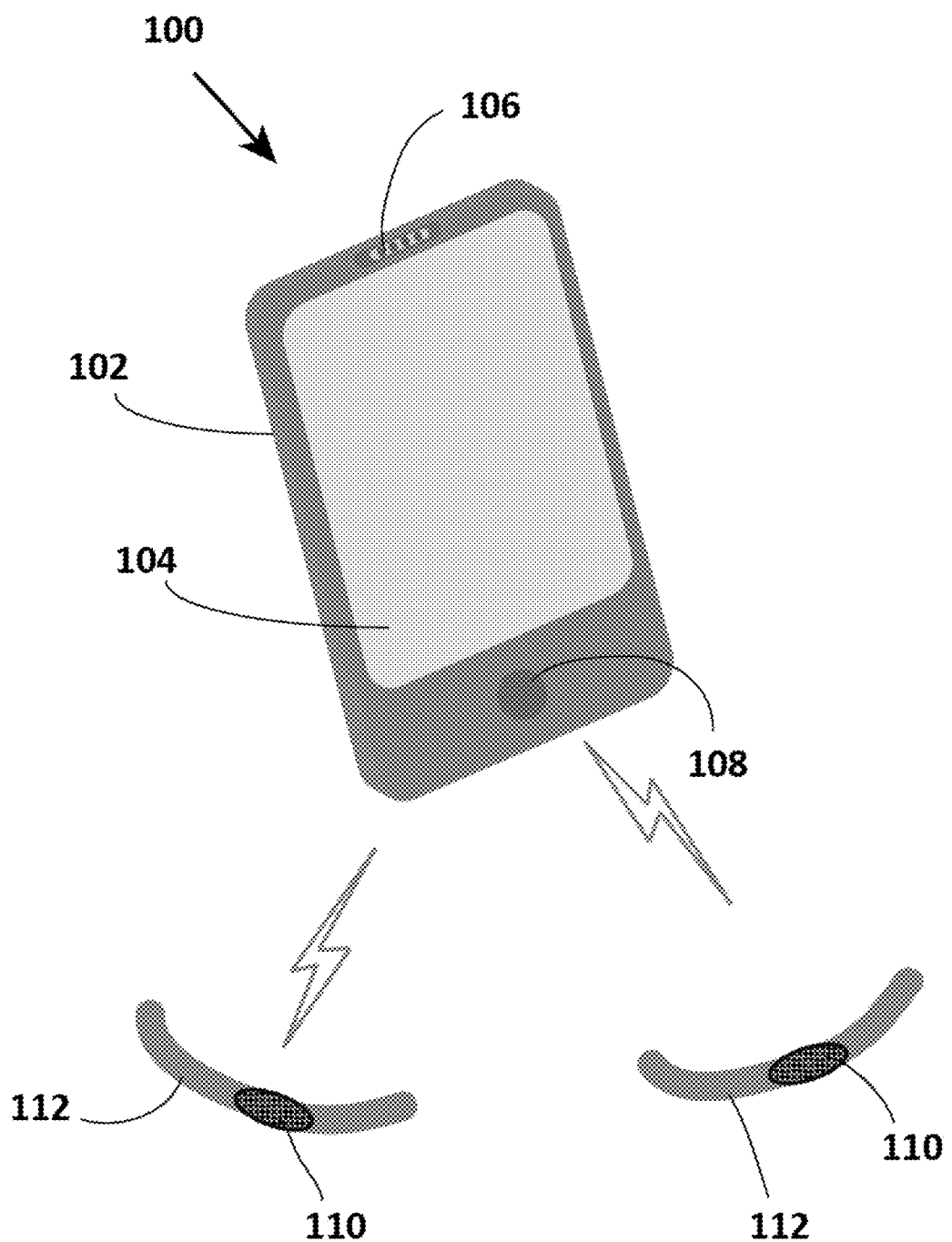
FIG. 1 is a perspective view of a medical device, according to one embodiment of the present invention, wherein the controller is in wireless communication with two patient worn modules, each comprising a stimulator and a physiological sensor, which are attached to separate belts.

FIG. 1 is a perspective view of one embodiment of the present invention. In this embodiment, a portable, battery powered controller 100 comprises a portable housing 102 containing electronic circuitry (not visible), which is coupled to two portable, battery powered, patient worn modules 110. The controller 100 contains a processor (not visible), which is coupled to a touch sensitive screen 104, a wired communication port 106, and, one or more wireless communication mechanisms (not visible).

The patient worn modules 110 each contain a processor (not visible), which is coupled to one or more wireless communication mechanisms (not visible), a stimulator (not visible) and one or more physiological sensors (not visible). The stimulator may optionally comprise a vibration motor, which may include an eccentric mass counter weight attached to the shaft of a circular motor, which when activated, causes a tactile stimulation when coupled to a patient. The stimulator may also optionally comprise a vibration motor, which may include a mass attached to the shaft of a linear motor, which when activated, causes a tactile stimulation when coupled to a patient. The stimulator may also optionally comprise a piezoelectric vibration motor, which when activated, causes a tactile stimulation when coupled to a patient. The stimulator may also optionally comprise a transcutaneous electrical nerve stimulator (TENS), which when activated, causes a neurological stimulation when coupled to a patient. The physiological sensors may optionally comprise one or more actimetry sensors, which detect gross motor movement when coupled to a patient. The patient worn modules 110 may periodically process data from the physiological sensors and transmit the resulting data to the controller 100 via the wireless communication mechanisms of each device. The patient worn modules 110 may be optionally attached to one or more adjustable belts 112.

The controller 100 is optionally coupled to two patient worn modules 110 through the wireless communication mechanisms of each device and controls the operation of the patient worn modules 110 to generate a repeating pattern of stimulation. The repeating pattern of stimulation has a first period of time when the stimulator of a first patient worn module 110 is activated followed by a second period of time when neither stimulator is activated, followed by a third period of time when the stimulator of a second patient worn module 110 is activated, followed by a fourth period of time when neither stimulator is activated.

The controller 100 may automatically adjust the characteristics of the repeating pattern of stimulation in response to physiological data received from the patient worn modules 110. The controller 100 may optionally automatically adjust the duration of time that each stimulator is active during each cycle of the repeating pattern of stimulation. The controller 100 may also optionally automatically adjust the duration of time that neither stimulator is active during each cycle of the repeating pattern of stimulation. The controller 100 may also optionally automatically adjust the relative intensity of the stimulations produced by each stimulator during each cycle of the repeating pattern of stimulation. The controller 100 may also optionally automatically terminate or initiate the repeating pattern of stimulation.

Variable controls may be presented in the user interface on the touch-sensitive screen 104 which allow the user to adjust the characteristics of the repeating pattern of stimulation. The user interface on the touch-sensitive screen 104 may optionally present a variable control, which the user may adjust to determine the duration of time that each stimulator is active during each cycle of the repeating pattern of stimulation. The duration of time that each stimulator is active during each cycle of the repeating pattern of stimulation may optionally be configured to a value between 10 milliseconds and 100 milliseconds, with a nominal value of 50 milliseconds. The duration of time that each stimulator is active during each cycle of the repeating pattern of stimulation may optionally be configured to a value between 100 milliseconds and 500 milliseconds, with a nominal value of 250 milliseconds. The duration of time that each stimulator is active during each cycle of the repeating pattern of stimulation may optionally be configured to a value between 500 milliseconds and 1000 milliseconds, with a nominal value of 750 milliseconds. The duration of time that each stimulator is active during each cycle of the repeating pattern of stimulation may optionally be configured to a value between 1000 milliseconds and 2000 milliseconds, with a nominal value of 1500 milliseconds. The duration of time that each stimulator is active during each cycle of the repeating pattern of stimulation may optionally be configured to a value between 2000 milliseconds and 3000 milliseconds, with a nominal value of 2500 milliseconds. The user interface on the touch-sensitive screen 104 may also optionally present a variable control, which the user may adjust to determine the duration of time that neither stimulator is active during each cycle of the repeating pattern of stimulation. The duration of time that neither stimulator is active during each cycle of the repeating pattern of stimulation may optionally be configured to a value between 10 milliseconds and 100 milliseconds, with a nominal value of 50 milliseconds. The duration of time that neither stimulator is active during each cycle of the repeating pattern of stimulation may optionally be configured to a value between 100 milliseconds and 500 milliseconds, with a nominal value of 250 milliseconds. The duration of time that neither stimulator is active during each cycle of the repeating pattern of stimulation may optionally be configured to a value between 500 milliseconds and 1000 milliseconds, with a nominal value of 750 milliseconds. The duration of time that neither stimulator is active during each cycle of the repeating pattern of stimulation may optionally be configured to a value between 1000 milliseconds and 2000 milliseconds, with a nominal value of 1500 milliseconds. The duration of time that neither stimulator is active during each cycle of the repeating pattern of stimulation may optionally be configured to a value between 2000 milliseconds and 3000 milliseconds, with a nominal value of 2500 milliseconds. The user interface on the touch-sensitive screen 104 may also optionally present a variable control, which the user may adjust to determine the relative intensity of the stimulations produced by each stimulator during each cycle of the repeating pattern of stimulation. The user interface on the touch-sensitive screen 104 may also optionally present a variable control, which the user may adjust to determine the length of time after which the controller 100 will terminate the repeating pattern of stimulation and to subsequently periodically monitor physiological data received from the patient worn modules 110 to determine if the patient is becoming aroused from sleep and to consequently resume the repeating pattern of stimulation. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 10 minutes and 20 minutes, with a nominal value of 15 minutes. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 20 minutes and 30 minutes, with a nominal value of 25 minutes. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 30 minutes and 40 minutes, with a nominal value of 35 minutes. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 40 minutes and 50 minutes, with a nominal value of 45 minutes. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 50 minutes and 60 minutes, with a nominal value of 55 minutes. The length of time after which the controller 100 will terminate the repeating pattern of stimulation and subsequently periodically monitor physiological data received from the patient worn modules 110 to determine if the patient is becoming aroused from sleep and consequently resume the repeating pattern of stimulation may optionally be configured to a value between 60 minutes and 90 minutes, with a nominal value of 75 minutes. The user interface on the touch-sensitive screen 104 may also optionally present a variable control, which the user may adjust to determine the length of time after which the controller 100 will terminate the repeating pattern of stimulation and will not periodically monitor physiological data received from the patient worn modules 110 to determine if the patient is becoming aroused from sleep. The length of time after which the controller 100 will terminate the repeating pattern of stimulation and will not periodically monitor physiological data received from the patient worn modules 110 to determine if the patient is becoming aroused from sleep may optionally be configured to a value between 10 minutes and 40 minutes, with a nominal value of 25 minutes. The length of time after which the controller 100 will terminate the repeating pattern of stimulation and will not periodically monitor physiological data received from the patient worn modules 110 to determine if the patient is becoming aroused from sleep may optionally be configured to a value between 40 minutes and 80 minutes, with a nominal value of 60 minutes. The length of time after which the controller 100 will terminate the repeating pattern of stimulation and will not periodically monitor physiological data received from the patient worn modules 110 to determine if the patient is becoming aroused from sleep may optionally be configured to a value between 80 minutes and 160 minutes, with a nominal value of 120 minutes. The length of time after which the controller 100 will terminate the repeating pattern of stimulation and will not periodically monitor physiological data received from the patient worn modules 110 to determine if the patient is becoming aroused from sleep may optionally be configured to a value between 160 minutes and 320 minutes, with a nominal value of 240 minutes. The length of time after which the controller 100 will terminate the repeating pattern of stimulation and will not periodically monitor physiological data received from the patient worn modules 110 to determine if the patient is becoming aroused from sleep may optionally be configured to a value between 320 minutes and 640 minutes, with a nominal value of 480 minutes. The length of time after which the controller 100 will terminate the repeating pattern of stimulation and will not periodically monitor physiological data received from the patient worn modules 110 to determine if the patient is becoming aroused from sleep may optionally be configured to a value between 480 minutes and 720 minutes, with a nominal value of 600 minutes.

Controls may be presented in the user interface on the touch-sensitive screen 104 which allow the user to select a preconfigured initial set of characteristics of the repeating pattern of stimulation including the duration of time that each stimulator is active during each cycle of the repeating pattern of stimulation, the duration of time that neither stimulator is active during each cycle of the repeating pattern of stimulation, the relative intensity of the stimulations, the length of time after which the controller 100 will terminate the repeating pattern of stimulation and subsequently periodically monitor physiological data received from the patient worn modules 110 to determine if the patient is becoming aroused from sleep and to consequently resume the repeating pattern of stimulation, and the length of time after which the controller 100 will terminate the repeating pattern of stimulation and will not periodically monitor physiological data received from the patient worn modules 110 to determine if the patient is becoming aroused from sleep.

In a typical context in which the controller 100 and two patient worn modules 110 are used, a patient prepares for sleep and attaches each patient worn module 110 to a separate adjustable belt 112, secures one adjustable belt around each wrist and applies power to each patient worn module 110 by activating a power control (not visible). The patient applies power to the controller 100 by activating control 108 and the controller establishes wireless communication with each of the patient worn modules using the wireless communication mechanisms of each device. The patient adjusts the previously mentioned controls on the touch sensitive screen 104 to set the initial characteristics of the repeating pattern of stimulation and the controller 100 initiates the repeating pattern of stimulation. The patient then attempts to initiate sleep. The controller 100 will terminate the repeating pattern of stimulation after the period of time set by the patient.

Subsequent to the initiation of the repeating pattern of stimulation, the processor in each patient worn module 110 periodically processes signals received from the actimetry sensors to generate relative position data, optionally stores this data in sequential order to create a sequential relative patient position data store, and optionally transmits this data to the controller 100 through the wireless communication mechanism of each device, wherein the controller 100 stores this data in sequential order to create a sequential relative patient position data store. The period of time between subsequent generations of relative patient position data may optionally be configured to a value between 1 and 120 seconds, with a nominal value of 60 seconds. The period of time between subsequent generations of relative patient position data may also optionally be configured to a value between 1 and 60 seconds, with a nominal value of 30 seconds. The period of time between subsequent generations of relative patient position data may also optionally be configured to a value between 1 and 30 seconds, with a nominal value of 10 seconds. The period of time between subsequent generations of relative patient position data may also optionally be configured to a value between 1 and 10 seconds, with a nominal value of 1 second.

The processor in each patient worn module 110 also optionally periodically processes the sequential relative patient position data store and generates data indicative of the number of gross motor movements experienced by the patient over a defined period of time, optionally stores this data in sequential order to create a sequential patient movement data store, and optionally transmits this data to the controller 100 through the wireless communication mechanism of each device, wherein the controller 100 stores this data in sequential order to create a sequential patient movement data store. Alternatively, the processor in the controller 100 periodically processes the sequential relative patient position data store and generates data indicative of the number of gross motor movements experienced by the patient over a defined period of time, and stores this data in sequential order to create a sequential patient movement data store. The defined period of time over which the number of gross motor movements experienced by the patient is determined, may optionally be configured to a value between 1 and 360 seconds, with a nominal value of 180 seconds. The defined period of time over which the number of gross motor movements experienced by the patient is determined, may also optionally be configured to a value between 1 and 240 seconds, with a nominal value of 120 seconds. The defined period of time over which the number of gross motor movements experienced by the patient is determined, may also optionally be configured to a value between 1 and 120 seconds, with a nominal value of 60 seconds. The defined period of time over which the number of gross motor movements experienced by the patient is determined, may also optionally be configured to a value between 1 and 60 seconds, with a nominal value of 30 seconds.

Optionally the processor in each patient worn module 110 and optionally the processor in the controller 100 compare sequential relative position data in the sequential relative patient position data store and determines that the patient has experienced a gross motor movement if the difference between the sequential relative positions exceeds a defined threshold. The defined threshold for determining that the patient has experienced a gross motor movement may optionally be configured to a value between 5 and 400 millimeters, with a nominal value of 200 millimeters. The defined threshold for determining that the patient has experienced a gross motor movement may also optionally be configured to a value between 5 and 200 millimeters, with a nominal value of 100 millimeters. The defined threshold for determining that the patient has experienced a gross motor movement may also optionally be configured to a value between 5 and 100 millimeters, with a nominal value of 50 millimeters. The defined threshold for determining that the patient has experienced a gross motor movement may also optionally be configured to a value between 5 and 50 millimeters, with a nominal value of 25 millimeters.

Additionally, subsequent to the initiation of the repeating pattern of stimulation, the processor in each patient worn module 110 also optionally periodically processes the sequential patient movement data store and generates data indicative of the wakefulness of the patient and stores this data in sequential order to create a sequential patient wakefulness data store, and optionally transmits this data to the controller 100 through the wireless communication mechanism of each device, wherein the controller 100 stores this data in sequential order to create a sequential patient wakefulness data store. Alternatively, the processor in the controller 100 periodically processes the sequential patient movement data store and generates data indicative of the wakefulness of the patient and stores this data in sequential order to create a sequential patient wakefulness data store. The period of time between subsequent generations of data indicative of the wakefulness of the patient may optionally be configured to a value between 1 and 360 seconds, with a nominal value of 180 seconds. The period of time between subsequent generations of data indicative of the wakefulness of the patient may also optionally be configured to a value between 1 and 240 seconds, with a nominal value of 120 seconds. The period of time between subsequent generations of data indicative of the wakefulness of the patient may also optionally be configured to a value between 1 and 120 seconds, with a nominal value of 60 seconds. The period of time between subsequent generations of data indicative of the wakefulness of the patient may also optionally be configured to a value between 1 and 60 seconds, with a nominal value of 30 seconds.

The processor in the controller 100 and optionally the processor in each patient worn module 110 compare the number of gross motor movements experienced by the patient over a defined period to a defined threshold to generate data indicative of the wakefulness of the patient. If the number of gross motor movements experienced by the patient over a defined period exceeds the defined threshold, the wakefulness of the patient is set to awake. If the number of gross motor movements experienced by the patient over a defined period is less than or equal to the defined threshold, the wakefulness of the patient is set to asleep. The defined threshold of gross motor movements experienced by the patient over a defined period for determining the wakefulness of the patient may optionally be configured to a value between 1 and 20 gross motor movements experienced by the patient over a defined period, with a nominal value of 10. The defined threshold of gross motor movements experienced by the patient over a defined period for determining the wakefulness of the patient may also optionally be configured to a value between 1 and 10 gross motor movements experienced by the patient over a defined period, with a nominal value of 5. The defined threshold of gross motor movements experienced by the patient over a defined period for determining the wakefulness of the patient may also optionally be configured to a value between 1 and 5 gross motor movements experienced by the patient over a defined period, with a nominal value of 2.

Additionally, subsequent to the initiation of the repeating pattern of stimulation, the processor in the controller 100 periodically processes the sequential patient wakefulness data store and generates a pattern of patient wakefulness. Optionally, subsequent to the initiation of the repeating pattern of stimulation, the processor in each patient worn module 110 periodically process the sequential patient wakefulness data store and generates a pattern of patient wakefulness and transmits this data to the controller 100 through the wireless communication mechanism of each device. The pattern of patient wakefulness may consist of a configurable number of the most recent data elements in the sequential patient wakefulness data store. The number of the most recent data elements in the sequential patient wakefulness data store used to generate the pattern of patient wakefulness may optionally be configured to a value between 1 and 30 elements with a nominal value of 15. The number of the most recent data elements in the sequential patient wakefulness data store used to generate the pattern of patient wakefulness may also optionally be configured to a value between 1 and 20 elements with a nominal value of 10. The number of the most recent data elements in the sequential patient wakefulness data store used to generate the pattern of patient wakefulness may also optionally be configured to a value between 1 and 10 elements with a nominal value of 5. The processor may also optionally modify the number of most recent data elements in the sequential patient wakefulness data store that is used to generate the pattern of patient wakefulness in response to values in the pattern of patient wakefulness. For example, if the pattern of patient wakefulness oscillates between states of asleep and awake, the processor may increase the number of most recent data elements in the sequential patient wakefulness data store that is used to generate the pattern of patient wakefulness.

The processor in the controller 100 may optionally modify the characteristics of the repeating pattern of stimulation in response to changes in the pattern of patient wakefulness. By way of example, if the percentage of data elements in the pattern of patient wakefulness indicating the patient is asleep increases between subsequent patterns of patient wakefulness, the processor may reduce the relative intensity of the stimulations of the repeating pattern of stimulation. By way of another example, if the percentage of data elements in the pattern of patient wakefulness indicating the patient is asleep exceeds a configurable threshold, the processor may terminate the repeating pattern of stimulation. By way of another example, if the repeating pattern of stimulation has been previously terminated and the percentage of data elements in the pattern of patient wakefulness indicating the patient is awake increases above a configurable threshold, the processor may re-initiate the repeating pattern of stimulation. By way of another example, if the repeating pattern of stimulation is currently active and the number of data elements in the pattern of patient wakefulness indicating the patient is awake, increases between subsequent patterns of patient wakefulness, the processor may optionally increase the relative intensify of the repeating pattern of stimulation.

FIG. 2 Description

Figure 2:
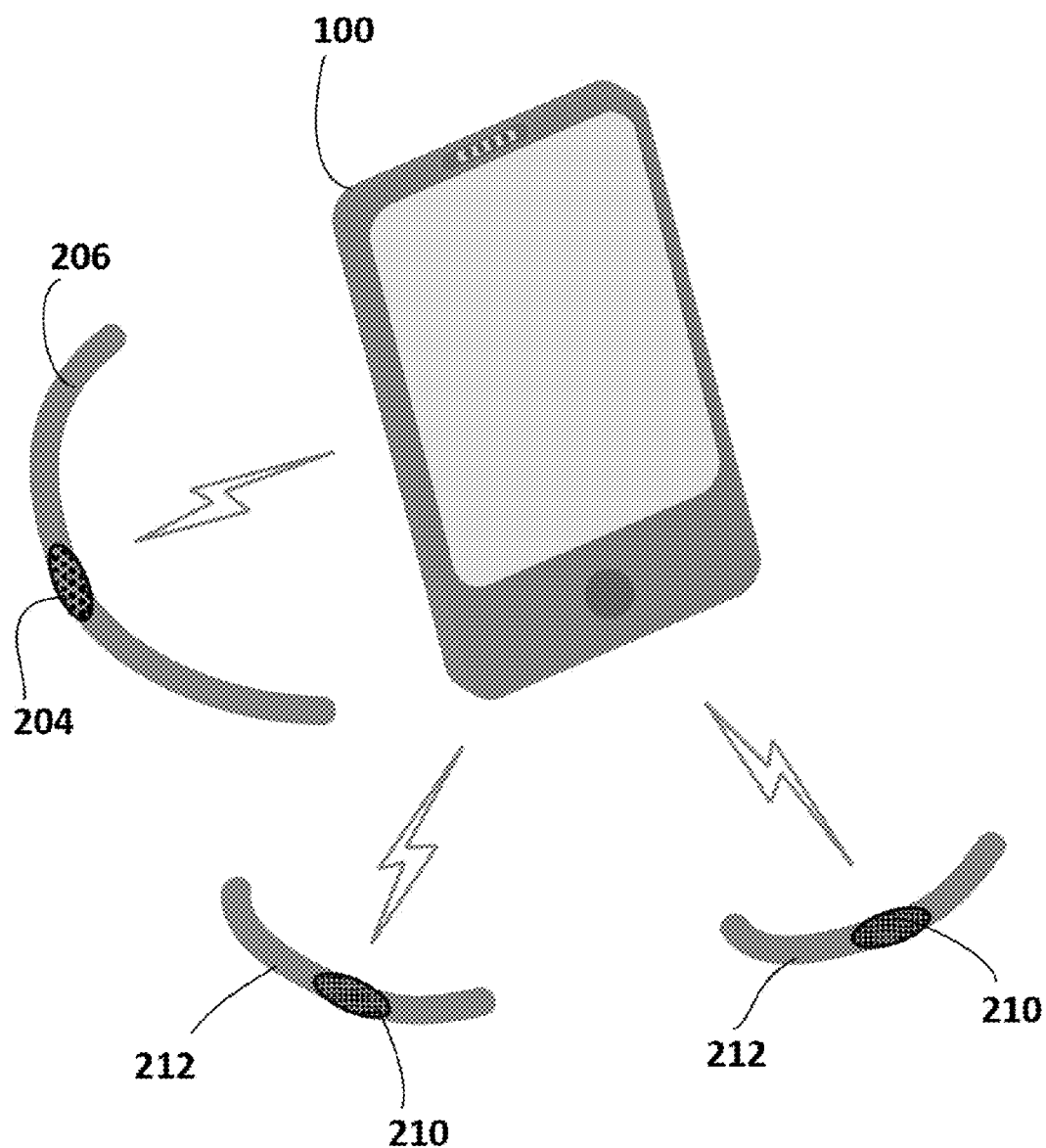
FIG. 2 is a perspective view of a medical device, according to a second embodiment of the present invention, wherein the controller is in wireless communication with two patient worn modules, each comprising a stimulator and a physiological sensor, which are attached to separate belts, and, the controller is in wireless communication with a third patient worn module comprising a physiological sensor, which is attached to a third belt.

FIG. 2 is a perspective view of a second embodiment of the present invention. In this embodiment a portable, battery powered controller 100 as previously described in FIG. 1 is coupled to two portable, battery powered, patient worn modules 210 and to one portable, battery powered, patient worn module 204.

The patient worn modules 210 each contain a processor (not visible), which is coupled to one or more wireless communication mechanisms (not visible), a stimulator (not visible) and one or more physiological sensors (not visible). The stimulator may optionally comprise an electroactive polymer, which responds to an induced electrical current by contracting, and which, when so activated, causes a tactile stimulation when coupled to a patient. The physiological sensors may optionally comprise one or more actimetry sensors, which detect gross motor movement when coupled to a patient. The processor in the patient worn modules 210 may periodically process data from the actimetry sensors and transmit the resulting data to the controller via the wireless communication mechanisms of each device. The patient worn modules 210 may be optionally attached to one or more adjustable belts 212.

The patient worn module 204 contains a processor (not visible), which is coupled to one or more wireless communication mechanisms (not visible), and one or more physiological sensors (not visible). The physiological sensors may optionally comprise a respiratory sensor, which measures the patient's respiration rate when coupled to the patient. The processor in the patient worn module 204 may periodically process data from the respiratory sensor and transmit the resulting data to the controller via the wireless communication mechanisms of each device. The patient worn module 204 may be optionally attached to an adjustable belt 206.

The controller 100 is optionally coupled to the two patient worn modules 210 through the wireless communication mechanisms of each device, and, the controller 100 is optionally coupled to the patient worn module 204 through the wireless communication mechanisms of each device.

The controller 100 controls the operation of the two patient worn modules 210 to generate a repeating pattern of stimulation. The repeating pattern of stimulation is as described previously in FIG. 1.

The controller 100 may automatically adjust the characteristics of the repeating pattern of stimulation in response to physiological data received from the patient worn modules 210 and 204. The controller 100 may optionally automatically adjust the duration of time that each stimulator is active during each cycle of the repeating pattern of stimulation. The controller 100 may also optionally automatically adjust the duration of time that neither stimulator is active during each cycle of the repeating pattern of stimulation. The controller 100 may also optionally automatically adjust the relative intensity of the stimulations produced by each stimulator during each cycle of the repeating pattern of stimulation. The controller 100 may also optionally automatically terminate or initiate the repeating pattern of stimulation.

Variable controls may be presented in the user interface on the controller 100, which control the initial characteristics of the repeating pattern of stimulation as described previously in FIG. 1.

Controls may also be presented in the user interface on the controller 100 which allow the user to select a preconfigured initial set of characteristics of the repeating pattern of stimulation as described previously in FIG. 1.

In a typical context in which the controller 100 and two patient worn modules 210, and, one patient worn module 204 are used, a patient prepares for sleep and attaches the patient worn module 204 to a single adjustable belt 206 and secures the adjustable belt around the patient's torso such that the module 204 is positioned to detect the patient's respiration rate. The patient also attaches each patient worn module 210 to separate adjustable belts 212, and secures one to each wrist as described previously in FIG. 1. The patient applies power to each of the patient worn modules 210 and 204 by activating a power control (not visible). The patient applies power to the controller 100 and the controller establishes wireless communication with each of the patient worn modules using the wireless communication mechanisms of each device. The patient adjusts the previously mentioned controls on the controller 100 to set the initial characteristics of the repeating pattern of stimulation, and initiates the repeating pattern of stimulation as described previously in FIG. 1. The patient then attempts to initiate sleep. The controller 100 will terminate the repeating pattern of stimulation after the period of time set by the patient as described previously in FIG. 1.

Subsequent to the initiation of the repeating pattern of stimulation, the processor in each patient worn module 210 periodically processes signals received from the actimetry sensor to generate data indicative of the relative patient position data, and optionally the number of gross motor movements experienced by the patient over a defined period of time, the wakefulness of the patient, and a pattern of patient wakefulness, and, transmits this data to the controller 100 through the wireless communication mechanisms of each device as described previously in FIG. 1.

Additionally, subsequent to the initiation of the repeating pattern of stimulation, the processor in the controller 100 periodically optionally processes the data received from each patient worn module 210 (e.g. indicative of the number of gross motor movements experienced by the patient over a defined period of time) and generates a pattern of patient wakefulness as described previously in FIG. 1. The processor in the controller 100 may optionally modify the characteristics of the repeating pattern of stimulation in response to changes in the pattern of patient wakefulness as described previously in FIG. 1.

Additionally, subsequent to the initiation of the repeating pattern of stimulation, the processor in the patient worn module 204 periodically processes signals received from the respiratory sensor, and generates data indicative of the patient's respiration rate, and transmits this data to the controller 100 through the wireless communication mechanism of each device.

Additionally, subsequent to the initiation of the repeating pattern of stimulation, the processor in the controller 100 periodically processes the data indicative of the patient's respiration rate and stores this data in sequential order to create a sequential patient respiration rate data store. The processor in the controller 100 periodically processes the sequential patient respiration rate data store and generates a pattern of patient respiration rate. The pattern of patient respiration rate may consist of a configurable number of the most recent data elements in the sequential patient respiration rate data store. The number of the most recent data elements in the sequential patient respiration rate data store used to generate the pattern of patient respiration rate may optionally be configured to a value between 1 and 30 elements with a nominal value of 15. The number of the most recent data elements in the sequential patient respiration rate data store used to generate the pattern of patient respiration rate may also optionally be configured to a value between 1 and 20 elements with a nominal value of 10. The number of the most recent data elements in the sequential patient respiration rate data store used to generate the pattern of patient respiration rate may also optionally be configured to a value between 1 and 10 elements with a nominal value of 5. The processor may also optionally modify the number of most recent data elements in the sequential patient respiration rate data store that is used to generate the pattern of patient respiration rate in response to values in the pattern of patient respiration rate. For example, if the pattern of patient respiration rate contains values that are erratic or otherwise not consistent between two or more sequential values, the processor may increase the number of most recent data elements in the sequential patient respiration rate data store that is used to generate the pattern of patient respiration rate.

It will be understood by one skilled in the art that the generation of the previously described physiological data, including the sequential patient respiration rate data store, and the pattern of patient respiration rate, may optionally be performed by the processor in the patient worn module 204 in coordination with the processor in the controller 100.

The processor in the controller 100 may optionally store one or more values of the patient respiration rate in long-term storage, which are available to the processor following subsequent cycling of power to the controller 100. The processor may store values of the patient respiration rate in long-term storage, which are indicative of the respiration rate of the patient corresponding to specific patterns of wakefulness that are described previously in FIG. 1. The processor in the controller 100 may optionally modify the characteristics of the repeating pattern of stimulation in response to the values in the pattern of patient respiration rate and the values of the patient respiration rate in long-term storage. By way of example, if the most recent pattern of patient respiration rate has an average value that exceeds the value of the patient respiration rate corresponding to a wakefulness state of asleep in long term storage, the controller 100 may optionally modify the characteristics of the repeating pattern of stimulation such that the rate of the repeating pattern of stimulation is a configurable percentage lower than the average value of the most recent pattern of patient respiration rate. The percentage by which the controller 100 modifies the rate of the repeating pattern of stimulation may be configured between 10% and 50% with a nominal value of 25%. The percentage by which the controller 100 modifies the rate of the repeating pattern of stimulation may also be optionally modified in response to the relative difference between the average value of the most recent pattern of patient respiration rate and the value of the patient respiration rate corresponding to a wakefulness state of asleep in long term storage.

It will be understood by one skilled in the art that the data used for comparison with the most recent pattern of patient respiration rate for purposes of modifying the characteristics of the repeating pattern of stimulation may derive from sources other than the patient. For example, rather than using values of the patient respiration rate corresponding to a specific state of wakefulness stored in long term storage, published data for normal patient respiration rate values corresponding to a specific state of wakefulness may be used.

FIG. 3 Description

Figure 3:
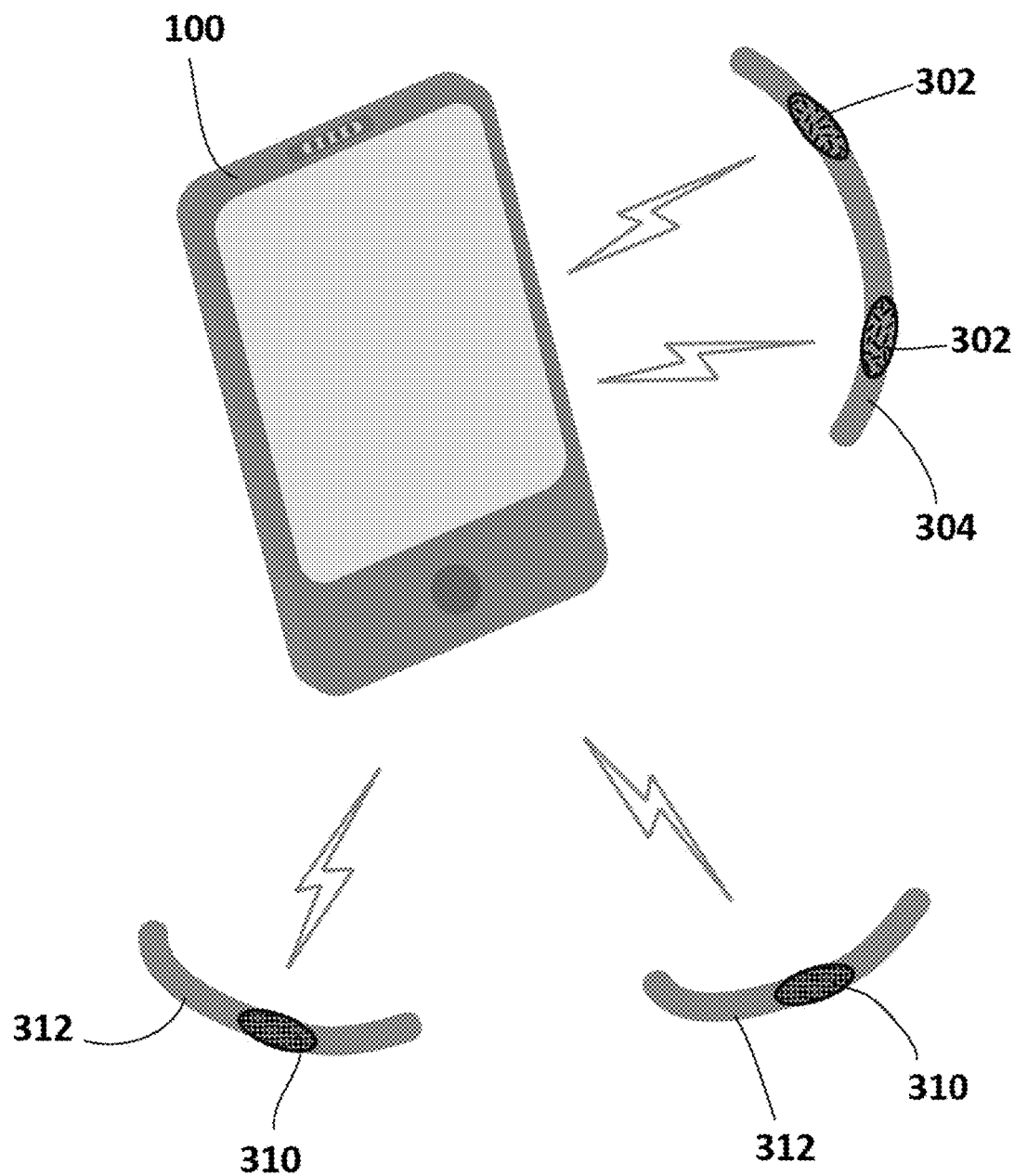
FIG. 3 is a perspective view of a medical device, according to a third embodiment of the present invention, wherein the controller is in wireless communication with two patient worn modules, each comprising a stimulator and a physiological sensor, which are attached to separate belts, and, the controller is in wireless communication with two additional patient worn modules comprising a physiological sensor, which are both attached to a third belt.

FIG. 3 is a perspective view of a third embodiment of the present invention. In this embodiment a portable, battery powered controller 100 as previously described in FIG. 1 is coupled to two portable, battery powered, patient worn modules 310 and to two portable, battery powered, patient worn modules 302.

The patient worn modules 310 each contain a processor (not visible), which is coupled to one or more wireless communication mechanisms (not visible), a stimulator (not visible) and one or more physiological sensors (not visible). The stimulator may optionally comprise one or more transcutaneous electrical nerve stimulators (TENS), which produce a mild electrical current, and which, when activated, cause a stimulation of the patient's nerves when coupled to a patient. The physiological sensors may optionally comprise one or more heart rate sensors, which detect the patient's heart rate when coupled to a patient. The processors in the patient worn modules 310 may periodically process data from the heart rate sensor and transmit the resulting data to the controller 100 via the wireless communication mechanisms of each device. The patient worn modules 310 may be optionally attached to one or more adjustable belts 312.

The patient worn modules 302 each contain a processor (not visible), which is coupled to one or more wireless communication mechanisms (not visible) and one or more physiological sensors (not visible). The physiological sensors may optionally comprise one or more Electroencephalography (EEG) sensors, which detect the patient's brain wave activity when coupled to a patient. The processors in the patient worn modules 302 may periodically process data from the EEG sensors and transmit the resulting data to the controller 100 via the wireless communication mechanisms of each device. The patient worn modules 302 may be optionally attached to a single adjustable belt 304.

The controller 100 is optionally coupled to the two patient worn modules 310 through the wireless communication mechanisms of each device, and, the controller 100 is optionally coupled to the two patient worn modules 302 through the wireless communication mechanisms of each device.

The controller 100 controls the operation of the two patient worn modules 310 to generate a repeating pattern of stimulation. The repeating pattern of stimulation is as described previously in FIG. 1.

The controller 100 may automatically adjust the characteristics of the repeating pattern of stimulation in response to physiological data received from the patient worn modules 310 and 302. The controller 100 may optionally automatically adjust the duration of time that each stimulator is active during each cycle of the repeating pattern of stimulation. The controller 100 may also optionally automatically adjust the duration of time that neither stimulator is active during each cycle of the repeating pattern of stimulation. The controller 100 may also optionally automatically adjust the relative intensity of the stimulations produced by each stimulator during each cycle of the repeating pattern of stimulation. The controller 100 may also optionally automatically terminate or initiate the repeating pattern of stimulation.

Variable controls may be presented in the user interface on the controller 100, which control the initial characteristics of the repeating pattern of stimulation as described previously in FIG. 1.

Controls may also be presented in the user interface on the controller 100 which allow the user to select a preconfigured initial set of characteristics of the repeating pattern of stimulation as described previously in FIG. 1.

In a typical context in which the controller 100 and two patient worn modules 310, and, two patient worn modules 302 are used, a patient prepares for sleep and attaches the patient worn modules 302 to a single adjustable belt 304 and secures the adjustable belt around the patient's head such that the patient worn modules 302 are positioned to detect the electrical activity of the patient's brain. The patient attaches each patient worn module 310 to a separate adjustable belt 312, and secures one to each wrist such that the heart rate sensors are positioned to detect the patient's heart rate and the TENS are positioned to provide electrical nerve stimulation, in one embodiment on the inside of the wrist. The patient applies power to each of the patient worn modules 310 and 302, by activating a control (not visible). The patient applies power to the controller 100 and the controller establishes wireless communication with each of the patient worn modules using the wireless communication mechanisms of each device. The patient adjusts the previously mentioned controls on the controller 100 to set the initial characteristics of the repeating pattern of stimulation, and initiates the repeating pattern of stimulation as described previously in FIG. 1. The patient then attempts to initiate sleep. The controller 100 will terminate the repeating pattern of stimulation after the period of time set by the patient as described previously in FIG. 1.

Subsequent to the initiation of the repeating pattern of stimulation, the processor in each patient worn module 302 periodically processes signals received from the EEG sensors and generates data indicative of the electrical activity of the patient's brain, and stores this data in sequential order to create a sequential patient brain electrical activity data store. Each processor periodically processes the sequential patient brain electrical activity data store and generates the spectral power density for multiple configurable frequency ranges, with four nominal frequency ranges defined as $0.5<\delta<4$ Hz, $4<\theta<8$ Hz, $8<\alpha<13.0$ Hz, $13.0<\beta<28.0$ Hz and transmits this data to the controller 100 through the wireless communication mechanisms of each device. The processor in each patient worn module 302 may optionally calculate the spectral power density using a Fast Fourier Transform.

The processor in the controller 100 stores the spectral power density data in sequential order to create a sequential spectral power density data store. Additionally, the processor in the controller 100 periodically processes the sequential spectral power density data store to compute the relative spectral power of each of the frequency ranges and stores this data in sequential order to create a sequential relative spectral power data store.

Additionally, the processor in the controller 100 periodically processes the sequential relative spectral power data store and generates a pattern of relative spectral power for each of the defined frequency ranges. The number of the most recent data elements in the sequential relative spectral power data store used to generate the pattern of relative spectral power may optionally be configured to a value between 1 and 30 elements with a nominal value of 15. The number of the most recent data elements in the sequential relative spectral power data store used to generate the pattern of relative spectral power may also optionally be configured to a value between 1 and 20 elements with a nominal value of 10. The number of the most recent data elements in the sequential relative spectral power data store used to generate the pattern of relative spectral power may also optionally be configured to a value between 1 and 10 elements with a nominal value of 5. The processor may also optionally modify the number of most recent data elements in the sequential relative spectral power data store that is used to generate the pattern of relative spectral power in response to values in the pattern of relative spectral power. For example, if the pattern of relative spectral power contains values that are erratic or otherwise not consistent between two or more sequential values, the processor may increase the number of most recent data elements in the sequential relative spectral power data store that is used to generate the pattern of relative spectral power.

Additionally, the processor in the controller 100 periodically compares the pattern of relative spectral power for each of the defined frequency ranges and generates data indicative of the wakefulness of the patient and stores this data in sequential order to create a sequential patient wakefulness data store. The period of time between subsequent generations of data indicative of the wakefulness of the patient may optionally be configured to a value between 1 and 360 seconds, with a nominal value of 180 seconds. The period of time between subsequent generations of data indicative of the wakefulness of the patient may also optionally be configured to a value between 1 and 240 seconds, with a nominal value of 120 seconds. The period of time between subsequent generations of data indicative of the wakefulness of the patient may also optionally be configured to a value between 1 and 120 seconds, with a nominal value of 60 seconds. The period of time between subsequent generations of data indicative of the wakefulness of the patient may also optionally be configured to a value between 1 and 60 seconds, with a nominal value of 30 seconds.

By way of example, if the relative spectral power for the $\theta$ range of frequencies is smaller than the relative spectral power for the $\delta$ frequency range the wakefulness of the patient is set to asleep, and, if the relative spectral power for the $\beta$ range of frequencies is larger than the relative spectral power for the $\delta$ frequency range the wakefulness of the patient is set to awake.

Additionally, subsequent to the initiation of the repeating pattern of stimulation, the processor in the controller 100 periodically compares the values in the patterns of relative spectral power for the frequency ranges and may optionally modify the characteristics of the repeating pattern of stimulation in response to these values.

By way of example, if the processor determines that the pattern of relative spectral power for the $\delta$ frequency range is increasing, and the pattern of relative spectral power for the $\alpha$ frequency range is decreasing, and the value of the most recent relative spectral power for the $\alpha$ range of frequencies is larger than the most recent value for the relative spectral power for the $\delta$ range of frequencies, indicating the patient may be approaching a sleep state, the controller 100 may optionally reduce the relative intensity of the stimulations of the repeating pattern of stimulation.

By way of another example, if the processor determines that the pattern of relative spectral power for the $\delta$ frequency range is increasing, and the pattern of relative spectral power for the $\alpha$ frequency range is decreasing, and the value of the most recent relative spectral power for the $\alpha$ range of frequencies is smaller than the most recent value for the relative spectral power for the $\delta$ range of frequencies, indicating the patient may be in a sleep state, the controller 100 may optionally terminate the repeating pattern of stimulations.

By way of another example, if the processor determines that the pattern of relative spectral power for the $\delta$ frequency range is increasing, and the pattern of relative spectral power for the $\theta$ frequency range is decreasing, and the value of the most recent relative spectral power for the $\theta$ range of frequencies is larger than the most recent value for the relative spectral power for the $\delta$ range of frequencies, indicating the patient may be approaching a sleep state, the controller 100 may optionally reduce the relative intensity of the stimulations of the repeating pattern of stimulation.

By way of another example, if the processor determines that the pattern of relative spectral power for the $\delta$ frequency range is increasing, and the pattern of relative spectral power for the $\theta$ frequency range is decreasing, and the value of the most recent relative spectral power for the $\theta$ range of frequencies is smaller than the most recent value for the relative spectral power for the $\delta$ range of frequencies, indicating the patient may be in a sleep state, the controller 100 may optionally terminate the repeating pattern of stimulations.

By way of another example, if the processor determines that the pattern of relative spectral power for the $\delta$ frequency range is increasing, and the pattern of relative spectral power for the $\beta$ frequency range is decreasing, and the value of the most recent relative spectral power for the $\beta$ range of frequencies is larger than the most recent value for the relative spectral power for the $\delta$ range of frequencies, indicating the patient may be approaching a sleep state, the controller 100 may optionally reduce the relative intensity of the stimulations of the repeating pattern of stimulation.

By way of another example, if the processor determines that the pattern of relative spectral power for the $\delta$ frequency range is increasing, and the pattern of relative spectral power for the $\beta$ frequency range is decreasing, and the value of the most recent relative spectral power for the $\beta$ range of frequencies is smaller than the most recent value for the relative spectral power for the $\delta$ range of frequencies, indicating the patient may be in a sleep state, the controller 100 may optionally terminate the repeating pattern of stimulation.

By way of another example, if the processor determines that the pattern of relative spectral power for the δ frequency range is decreasing, and the pattern of relative spectral power for the β frequency range is increasing, and the value of the most recent relative spectral power for the β range of frequencies is smaller than the most recent value for the relative spectral power for the δ range of frequencies, indicating the patient may becoming aroused from sleep, the controller 100 may optionally re-initiate the repeating pattern of stimulation.

By way of another example, if the processor determines that the pattern of relative spectral power for the δ frequency range is decreasing, and the pattern of relative spectral power for the β frequency range is increasing, and the value of the most recent relative spectral power for the β range of frequencies is larger than the most recent value for the relative spectral power for the δ range of frequencies, indicating the patient may have awakened from sleep, the controller 100 may optionally increase the relative intensity of the stimulations of the repeating pattern of stimulation.

The processor may optionally store one or more values of the patient spectral power density data in long term storage, which is available to the processor following subsequent cycling of power to the controller 100. The processor may store values of the spectral power density data in long-term storage, which are indicative of the spectral power density data of the patient corresponding to specific patterns of wakefulness that are described previously. The controller 100 may optionally modify the characteristics of the repeating pattern of stimulation in response to the values in the pattern of patient spectral power density data and the values of the patient spectral power density data corresponding to specific patterns of wakefulness in long-term storage. By way of example, if the most recent pattern of patient spectral power density data begins to approximate the patient spectral power density data corresponding to a wakefulness state of asleep in long term storage, the controller 100 may reduce the relative intensity of the stimulations of the repeating pattern of stimulation. By way of another example, if the most recent pattern of patient spectral power density data approximates the patient spectral power density data corresponding to a wakefulness state of asleep in long term storage, the processor may terminate the repeating pattern of stimulation.

It will be understood by one skilled in the art that the data used for comparison with the most recent pattern of patient spectral power density data for purposes of modifying the characteristics of the repeating pattern of stimulation may derive from sources other than the patient. For example, rather than using values of the patient spectral power density data corresponding to a specific state of wakefulness stored in long term storage, published data for normal patient spectral power density values corresponding to a specific state of wakefulness may be used.

It will be understood by one skilled in the art that the generation of the previously described physiological data, including the sequential patient brain electrical activity data store, the spectral power density for multiple configurable frequency ranges, the sequential spectral power density data store, the sequential relative spectral power data store, the pattern of relative spectral power for each of the defined frequency ranges, and, the sequential patient wakefulness data store may optionally be performed by the processor in each of the patient worn modules 302 in coordination with the processor in the controller 100.

Additionally, subsequent to the initiation of the repeating pattern of stimulation, the processor in the patient worn module 310 periodically processes signals received from the heart rate sensor, and generates data indicative of the patient's heart rate, and transmits this data to the controller 100 through the wireless communication mechanisms of each device.

Additionally, subsequent to the initiation of the repeating pattern of stimulation, the processor in the controller 100 periodically processes the data indicative of the patient's heart rate and stores this data in sequential order to create a sequential patient heart rate data store. The processor in the controller 100 periodically processes the sequential patient heart rate data store and generates a pattern of patient heart rate. The pattern of patient heart rate may consist of a configurable number of the most recent data elements in the sequential patient heart rate data store. The number of the most recent data elements in the sequential patient heart rate data store used to generate the pattern of patient heart rate may optionally be configured to a value between 1 and 30 elements with a nominal value of 15. The number of the most recent data elements in the sequential patient heart rate data store used to generate the pattern of patient heart rate may also optionally be configured to a value between 1 and 20 elements with a nominal value of 10. The number of the most recent data elements in the sequential patient heart rate data store used to generate the pattern of patient heart rate may also optionally be configured to a value between 1 and 10 elements with a nominal value of 5. The processor may also optionally modify the number of most recent data elements in the sequential patient heart rate data store that is used to generate the pattern of patient heart rate in response to values in the pattern of patient heart rate. For example, if the pattern of heart rate contains values that are erratic or otherwise not consistent between two or more sequential values, the processor may increase the number of most recent data elements in the sequential heart rate data store that is used to generate the pattern of heart rate.

The processor may optionally store one or more values of the patient heart rate in long term storage, which is available to the processor following subsequent cycling of power to the controller 100. The processor may store values of the patient heart rate in long-term storage, which are indicative of the heart rate of the patient corresponding to specific patterns of wakefulness that are described previously. The controller 100 may optionally modify the characteristics of the repeating pattern of stimulation in response to the values in the pattern of patient heart rate and the values of the patient heart rate corresponding to specific patterns of wakefulness in long-term storage. By way of example, if the most recent pattern of patient heart rate indicates the patient heart rate is decreasing and has an average value larger than the value of the patient heart rate corresponding to a wakefulness state of asleep in long term storage, the controller 100 may reduce the relative intensity of the stimulations of the repeating pattern of stimulation. By way of another example, if the most recent pattern of patient heart rate indicates the patient heart rate is decreasing and has an average value less than or equal to the value of the patient heart rate corresponding to a wakefulness state of asleep in long term storage, the processor may terminate the repeating pattern of stimulation.

It will be understood by one skilled in the art that the data used for comparison with the most recent pattern of patient heart rate for purposes of modifying the repeating pattern of stimulation may derive from sources other than the patient. For example, rather than using values of the patient heart rate corresponding to a specific state of wakefulness stored in long term storage, published data for normal patient heart rate values corresponding to a specific state of wakefulness may be used.

It will be understood by one skilled in the art that the generation of the previously described physiological data, including the sequential patient heart rate data store, and the pattern of patient heart rate, may optionally be performed by the processor in each of the patient worn modules 310 in coordination with the processor in the controller 100.

FIG. 4 Description

Figure 4:
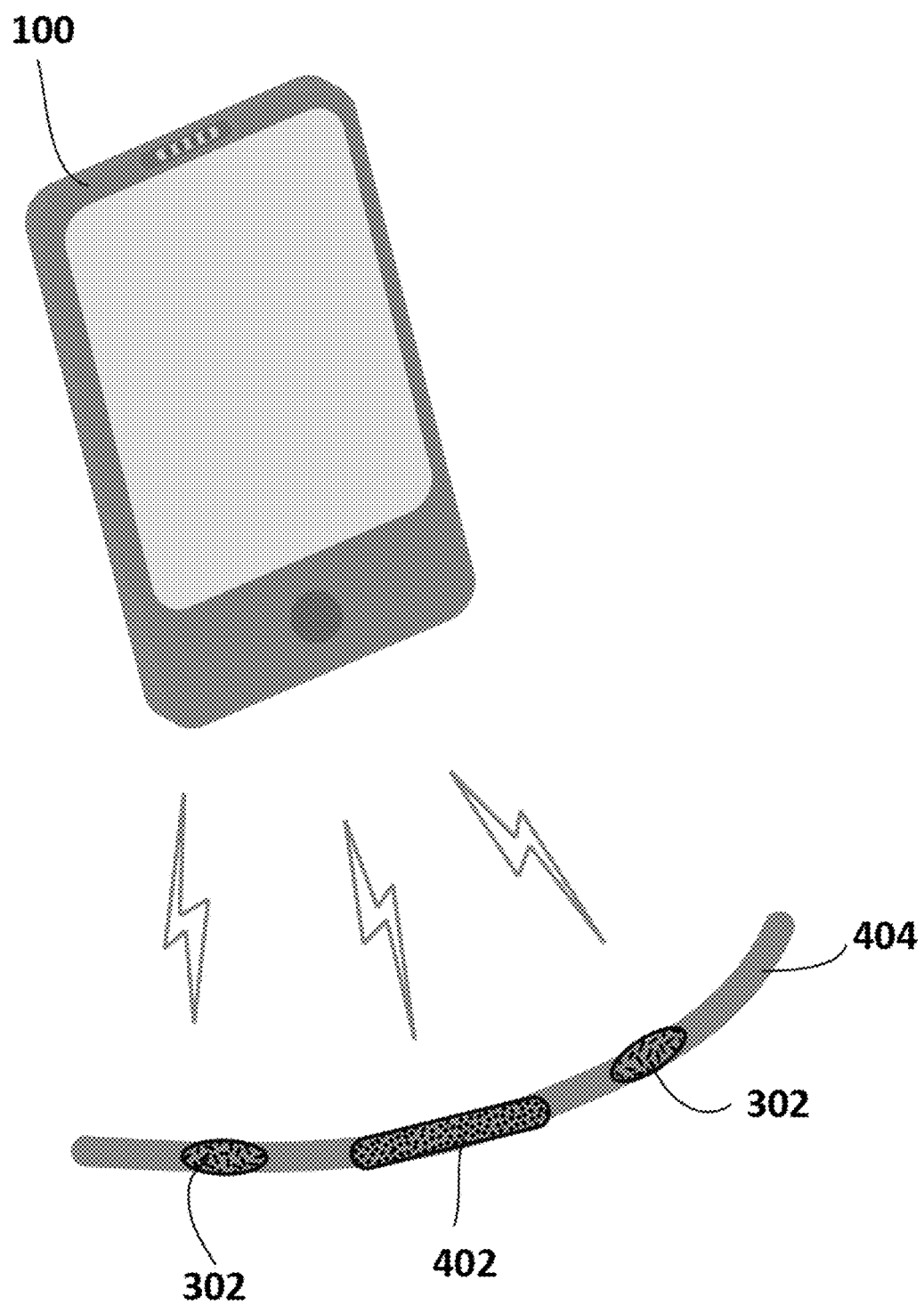
FIG. 4 is a perspective view of a medical device, according to a fourth embodiment of the present invention, wherein the controller is in wireless communication with two patient worn modules, each comprising a physiological sensor, and, the controller is in wireless communication with a third patient worn module comprising multiple stimulators, wherein all patient worn modules are attached to the same belt.

FIG. 4 is a perspective view of a fourth embodiment of the present invention. In this embodiment a portable, battery powered controller 100 as previously described in FIG. 1 is coupled to two portable, battery powered, patient worn modules 302 and to one portable, battery powered, patient worn module 402.

The patient worn modules 302 are the same as described previously in FIG. 3.

The patient worn modules 402 each contain a processor (not visible), which is coupled to one or more wireless communication mechanisms (not visible), and a stimulator (not visible). The stimulator may optionally comprise multiple light emitting diodes (LEDs) arranged in a horizontal array, which when energized create a visual stimulation when coupled to a patient.

The patient worn module 402, and the patient worn modules 302, may be optionally attached to a single adjustable belt 404.

The controller 100 is optionally coupled to the two patient worn modules 302 through the wireless communication mechanisms of each device, and, the controller 100 is optionally coupled to the patient worn module 402 through the wireless communication mechanisms of each device.

The controller 100 controls the operation of the patient worn module 402 to generate a repeating pattern of stimulation by energizing and de-energizing the LEDs sequentially from one end of the array to the other, pausing for a period of time and then energizing and de-energizing the LEDs sequentially in the reverse order, and then pausing for a period of time before repeating the entire sequence. The repeating pattern of stimulation is controlled as described previously in FIG. 1.

The controller 100 may automatically adjust the characteristics of the repeating pattern of stimulation in response to physiological data received from the patient worn modules 302 as described previously in FIG. 3. The controller 100 may optionally automatically adjust the duration of time for the LEDs to energize and de-energize sequentially from one end of the array to the other during each cycle of the repeating pattern of stimulation. The controller 100 may also optionally automatically adjust the duration of time to pause between energizing and de-energizing the LEDS from one end of the array to the other during each cycle of the repeating pattern of stimulation. The controller 100 may also optionally automatically adjust the relative intensity of the brightness produced by each LED during each cycle of the repeating pattern of stimulation. The controller 100 may also optionally automatically terminate or initiate the repeating pattern of stimulation.

Variable controls may be presented in the user interface on the controller 100, which control the initial characteristics of the repeating pattern of stimulation as described previously in FIG. 1.

Controls may also be presented in the user interface on the controller 100 which allow the user to select a preconfigured initial set of characteristics of the repeating pattern of stimulation as described previously in FIG. 1.

In a typical context in which the controller 100 and patient worn module 402, and, two patient worn modules 302 are used, a patient prepares for sleep and attaches the patient worn modules 302 and patient worn module 402 to a single adjustable belt 404 and secures the adjustable belt around the patient's head such that the patient worn modules 302 are positioned to detect the electrical activity of the patient's brain, and the patient worn module 402 is positioned such that the horizontal array of LEDs is over the patient's eyes and centered horizontally over the patient's nose. The patient applies power to the patient worn modules 402 and 302 by activating a power control (not visible). The patient applies power to the controller 100 and the controller establishes wireless communication with each of the patient worn modules using the wireless communication mechanisms of each device. The patient adjusts the previously mentioned controls on the controller 100 to set the initial characteristics of the repeating pattern of stimulation, and initiates the repeating pattern of stimulation as described previously in FIG. 1. The patient then attempts to initiate sleep. The controller 100 will terminate the repeating pattern of stimulation after the period of time set by the patient as described previously in FIG. 1.

Subsequent to the initiation of the repeating pattern of stimulation, the processor in each patient worn module 302 periodically processes signals received from the EEG sensors and generates the spectral power density for multiple configurable frequency ranges as described previously in FIG. 3, and transmits this data to the controller 100 through the wireless communication mechanisms of each device. The processor in the controller 100 processes this data and generates a sequential relative spectral power data store, patterns of relative spectral power for the frequency ranges, and a sequential patient wakefulness data store as described previously in FIG. 3. Additionally, the processor in the controller 100 periodically processes the sequential relative spectral power data store and compares the values in the patterns of relative spectral power for the frequency ranges, and may optionally modify the characteristics of the repeating pattern of stimulation in response to these values in the same manner as previously described in FIG. 3.

FIG. 5 Description

Figure 5:
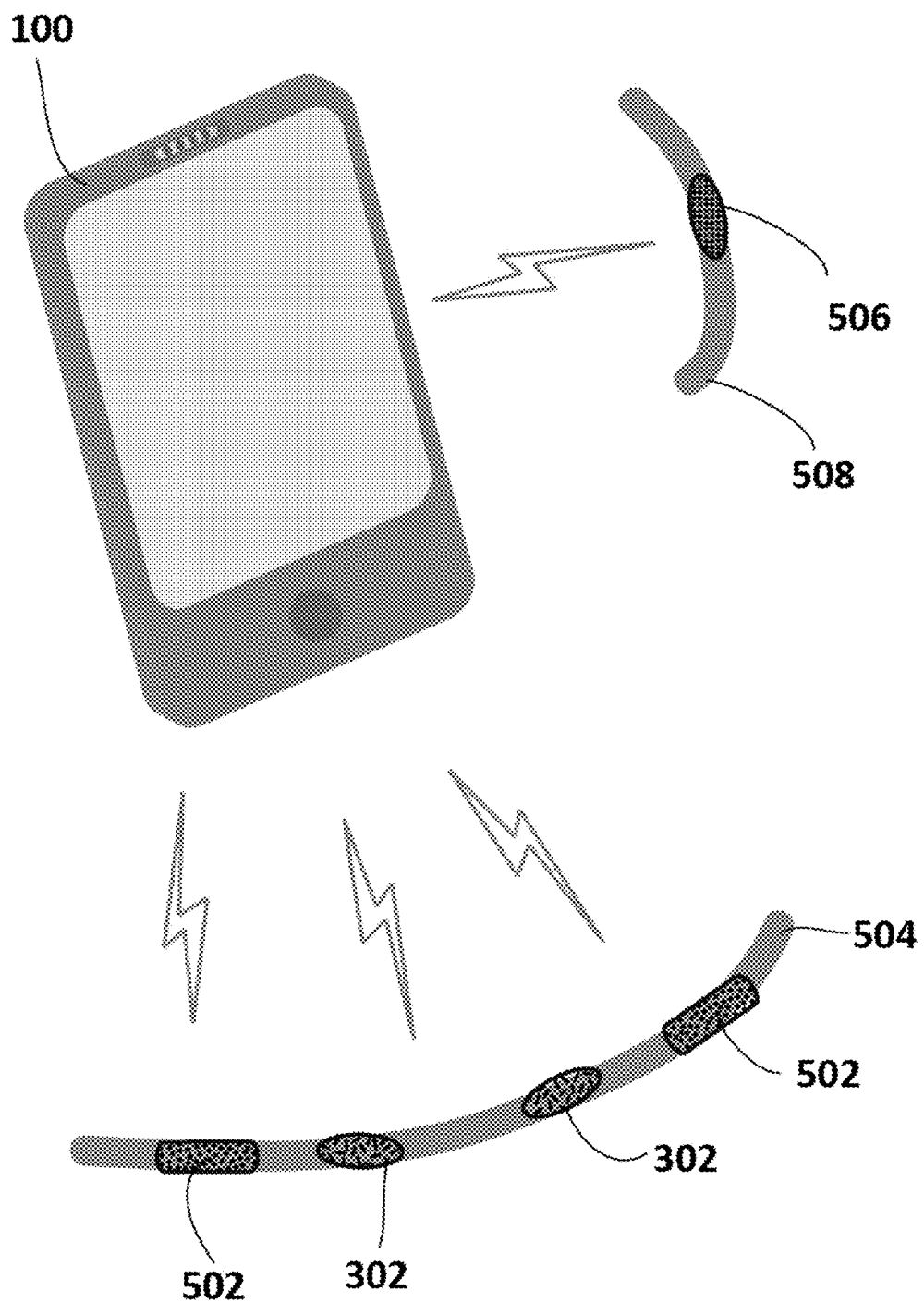
FIG. 5 is a perspective view of a medical device, according to a fifth embodiment of the present invention, wherein the controller is in wireless communication with two patient worn modules, each comprising a physiological sensor, and, the controller is in wireless communication with two additional patient worn modules each comprising a stimulator, wherein all four patient worn modules are attached to the same belt, and, the controller is in wireless communication with a fifth patient worn module comprising a physiological sensor which is attached to a second belt.

FIG. 5 is a perspective view of a fifth embodiment of the present invention. In this embodiment a portable, battery powered controller 100 as previously described in FIG. 1 is coupled to two portable, battery powered, patient worn modules 302, to two portable, battery powered, patient worn modules 502, and to one portable, battery powered, patient worn module 506.

The patient worn modules 302 are the same as described previously in FIG. 3.

The patient worn modules 502 each contain a processor (not visible), which is coupled to one or more wireless communication mechanisms (not visible), and a stimulator (not visible). The stimulator may optionally comprise one or more acoustic audio transducers, which when activated create an audible stimulation when coupled to a patient.

The patient worn modules 502 and the patient worn modules 302 may be optionally attached to a single adjustable belt 504.

The patient worn module 506 contains a processor (not visible), which is coupled to one or more wireless communication mechanisms (not visible), and one or more physiological sensors (not visible). The physiological sensors may optionally comprise a body temperature sensor, which measures the patient's body temperature when coupled to the patient. The processor in the patient worn module 506 may periodically process data from the body temperature sensor and transmit the resulting data to the controller via the wireless communication mechanisms of each device. The patient worn module 506 may be optionally attached to an adjustable belt 508.

The controller 100 is optionally coupled to the two patient worn modules 302 through the wireless communication mechanisms of each device, and, the controller 100 is optionally coupled to the patient worn modules 502 through the wireless communication mechanisms of each device, and the controller 100 is optionally coupled to the patient worn module 506 through the wireless communication mechanisms of each device.

The controller 100 controls the operation of the patient worn modules 502 to generate a repeating pattern of stimulation. The repeating pattern of stimulation is as described previously in FIG. 1.

The controller 100 may automatically adjust the characteristics of the repeating pattern of stimulation in response to physiological data received from the patient worn modules 302 and 506. The controller 100 may optionally automatically adjust the duration of time that each stimulator is active during each cycle of the repeating pattern of stimulation. The controller 100 may also optionally automatically adjust the duration of time that neither stimulator is active during each cycle of the repeating pattern of stimulation. The controller 100 may also optionally automatically adjust the relative intensity of the stimulations produced by each stimulator during each cycle of the repeating pattern of stimulation. The controller 100 may also optionally automatically terminate or initiate the repeating pattern of stimulation.

Variable controls may be presented in the user interface on the controller 100, which control the initial characteristics of the repeating pattern of stimulation as described previously in FIG. 1.

Controls may also be presented in the user interface on the controller 100 which allow the user to select a preconfigured initial set of characteristics of the repeating pattern of stimulation as described previously in FIG. 1.

In a typical context in which the controller 100 and two patient worn modules 502, and, two patient worn modules 302 and, one patient worn module 506 are used, a patient prepares for sleep and attaches the patient worn modules 302 and patient worn modules 502 to a single adjustable belt 504 and secures the belt around the patient's head such that the patient worn modules 302 are positioned to detect the electrical activity of the patient's brain, and the patient worn modules 502 are each positioned over one of the patient's ears. The patient attaches the patient worn modules 506 to an adjustable belt 508 and secures the adjustable belt around the patient's wrist such that the patient worn module 506 is positioned to detect the patient's body temperature. The patient applies power to each of the patient worn modules 502, 302 and 506 by activating a control (not visible). The patient applies power to the controller 100 and the controller establishes wireless communication with each of the patient worn modules using the wireless communication mechanisms of each device. The patient adjusts the previously mentioned controls on the controller 100 to set the initial characteristics of the repeating pattern of stimulation, and initiates the repeating pattern of stimulation as described previously in FIG. 1. The patient then attempts to initiate sleep. The controller 100 will terminate the repeating pattern of stimulation after the period of time set by the patient as described previously in FIG. 1.

Subsequent to the initiation of the repeating pattern of stimulation, the processor in each patient worn module 302 periodically processes signals received from the EEG sensors and generates the spectral power density for multiple configurable frequency ranges as described previously in FIG. 3, and transmits this data to the controller 100 through the wireless communication mechanisms of each device. The processor in the controller 100 processes this data and generates a sequential relative spectral power data store, patterns of relative spectral power for the frequency ranges, and a sequential patient wakefulness data store as described previously in FIG. 3. Additionally, the processor in the controller 100 periodically processes the sequential relative spectral power data store and compares the values in the patterns of relative spectral power for the frequency ranges, and may optionally modify the characteristics of the repeating pattern of stimulation in response to these values in the same manner as previously described in FIG. 3.

Additionally, subsequent to the initiation of the repeating pattern of stimulation, the processor in the patient worn module 506 periodically processes signals received from the body temperature sensor, and generates data indicative of the patient's body temperature, and transmits this data to the controller 100 through the wireless communication mechanism of each device.

Additionally, subsequent to the initiation of the repeating pattern of stimulation, the processor in the controller 100 periodically processes the data indicative of the patient's body temperature and stores this data in sequential order to create a sequential patient body temperature data store. The processor in the controller 100 periodically processes the sequential patient body temperature data store and generates a pattern of patient body temperature. The pattern of patient body temperature may consist of a configurable number of the most recent data elements in the sequential patient body temperature data store. The number of the most recent data elements in the sequential patient body temperature data store used to generate the pattern of patient body temperature may optionally be configured to a value between 1 and 30 elements with a nominal value of 15. The number of the most recent data elements in the sequential patient body temperature data store used to generate the pattern of patient body temperature may also optionally be configured to a value between 1 and 20 elements with a nominal value of 10. The number of the most recent data elements in the sequential patient body temperature data store used to generate the pattern of patient body temperature may also optionally be configured to a value between 1 and 10 elements with a nominal value of 5. The processor may also optionally modify the number of most recent data elements in the sequential patient body temperature data store that is used to generate the pattern of patient body temperature in response to values in the pattern of patient body temperature. For example, if the pattern of body temperature contains values that are erratic or otherwise not consistent between two or more sequential values, the processor may increase the number of most recent data elements in the sequential body temperature data store that is used to generate the pattern of body temperature.

The processor in the controller 100 may optionally store one or more values of the patient body temperature in long-term storage, which is available to the processor following subsequent cycling of power to the controller 100. The processor may store values of the patient body temperature in long-term storage, which are indicative of the patient's body temperature corresponding to specific patterns of wakefulness that are described previously. The processor in the controller 100 may optionally modify the characteristics of the repeating pattern of stimulation in response to the values in the pattern of patient body temperature and the values of the patient body temperature in long-term storage. By way of example, if the most recent pattern of patient body temperature indicates the patient body temperature is decreasing and has an average value larger than the value of the patient body temperature corresponding to a wakefulness state of asleep in long term storage, the controller 100 may reduce the relative intensity of the stimulations of the repeating pattern of stimulation. By way of another example, if the most recent pattern of patient body temperature indicates the patient body temperature is decreasing and has an average value smaller than the value of the patient body temperature corresponding to a wakefulness state of asleep in long term storage, the controller 100 may terminate the repeating pattern of stimulation.

It will be understood by one skilled in the art that the data used for comparison with the most recent pattern of patient body temperature for purposes of modifying the characteristics of the repeating pattern of stimulation may derive from sources other than the patient. For example, rather than using values of the patient body temperature corresponding to a specific state of wakefulness stored in long term storage, published data for normal patient body temperature values corresponding to a specific state of wakefulness may be used.

Alternatively, the patient worn module 506 may optionally comprise a blood pressure sensor, which measures the patient's blood pressure when coupled to the patient. The processor in the patient worn device 506 and the processor in the controller 100 both process data derived from the blood pressure sensor in the same manner as described for the body temperature sensor. The controller 100 may optionally modify the characteristics of the repeating pattern of stimulation in response to this data in the same manner as described for the body temperature sensor.

FIG. 6 Description

Figure 6:
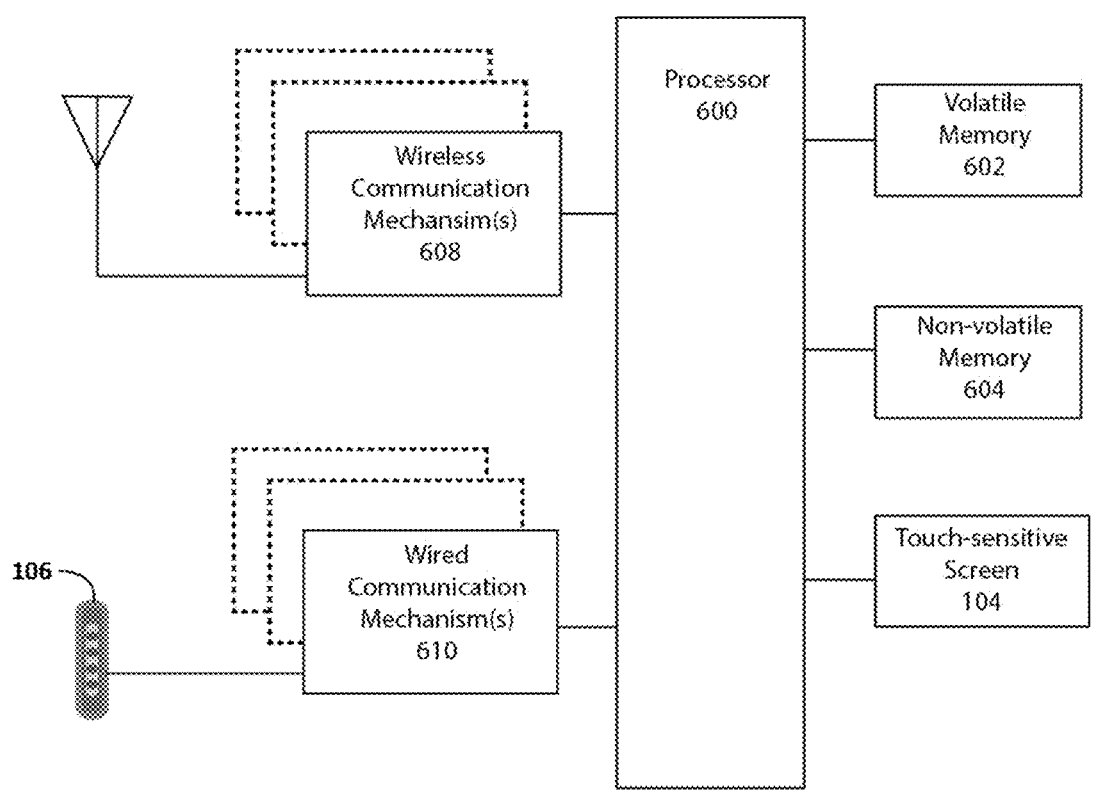
FIG. 6 is a block diagram of the controller of FIG. 1, according to one embodiment of the present invention, wherein the controller is comprised of a processor, memory, a touch sensitive screen, and wired and wireless communication mechanisms.

FIG. 6 is a block diagram of the controller 100 of FIG. 1. The block diagram shows the touch-sensitive screen 104 and the wireless communication mechanisms 608 described previously and other devices that are not visible in FIG. 1 such as the processor 600, volatile memory 602, non-volatile memory 604, and wired communication mechanisms 610.

The controller 100 may include one or more types of memory. For example, a non-volatile memory 604, such as a flash memory, may be used to store instructions for the processor while the controller 100 is powered down. When the controller 100 is powered on, these instructions may be copied to a faster, volatile memory 602, such as synchronous dynamic random access memory (SDRAM) by a basic input/output system (BIOS) or the like. Once the volatile memory 602 is loaded with instructions, the processor 600 executes the instructions stored in the volatile memory 602. These instructions control the operation of the processor 600; that is, the processor 600 is programmed by these instructions to perform the operations described herein.

The non-volatile memory 604 may also store data while the controller 100 is powered down, so if the battery becomes exhausted, this data will be available after the battery is recharged or replaced. The processor 600 may optionally store configuration settings for the controls that determine the characteristics of the repeating pattern of stimulation in the non-volatile memory 604. The processor 600 may also optionally store data in the non-volatile memory 604, which are indicative of the respiration rate of the patient corresponding to specific patterns of wakefulness as described in FIG. 2. The processor 600 may also optionally store data in the non-volatile memory 604, which are indicative of the heart rate of the patient corresponding to specific patterns of wakefulness as described in FIG. 3. The processor 600 may also optionally store data in the non-volatile memory 604, which are indicative of the spectral power density data of the patient corresponding to specific patterns of wakefulness as described in FIG. 3. The processor 600 may also optionally store data in the non-volatile memory 604, which are indicative of the body temperature of the patient corresponding to specific patterns of wakefulness as described in FIG. 5. The processor 600 may also optionally store data in the non-volatile memory 604, which are indicative of the blood pressure of the patient corresponding to specific patterns of wakefulness as described in FIG. 5.

The controller 100 may include one or more wired communication mechanisms 610, which may be coupled to a wired communication port 106. The wired communication port 106 may be coupled to external computer systems using suitable wired communication devices. The processor 600 may communicate with external computer systems and may exchange data with those systems. The processor 600 may optionally transmit data stored in non-volatile memory 604, or volatile memory 602 to external computer systems for purposes of analysis. The processor 600 may also optionally receive data from external computer systems and store this data in non-volatile memory 604 or volatile memory 602. For example, said data may be used to change the default configuration characteristics of the repeating pattern of stimulation. The processor 600 may also optionally receive instructions from external computer systems that it stores in non-volatile memory 604 which may be used to control the operation of the processor 600 as described previously.

Although not shown in FIG. 6, the controller 100 may include a bus to interconnect the processor 600 and the touch-sensitive screen 104, the wireless communication mechanisms 608, the non-volatile memory 604 the volatile memory 602, and the wired communication mechanisms 610. The controller 100 may also include other circuits (not shown) to automatically connect the battery, processor 600 and other components.

FIG. 7 Description

Figure 7:
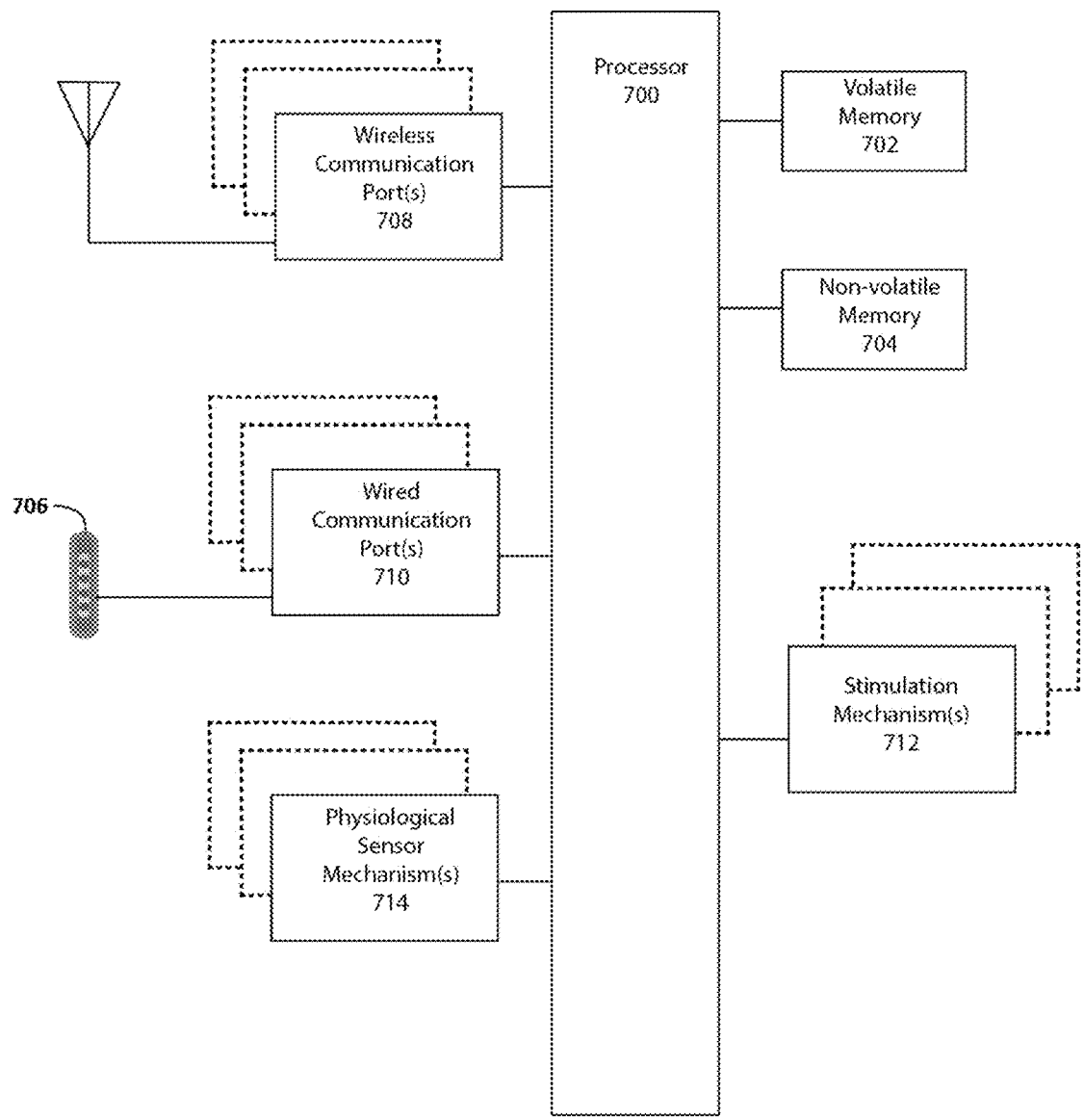
FIG. 7 is a block diagram of the patient worn modules of FIG. 1-6, according to one embodiment of the present invention, wherein the patient worn module is comprised of a processor, memory, wired and wireless communication mechanisms, zero or more stimulators and zero or more physiological sensors.

FIG. 7 is a block diagram of the patient worn modules described previously. The block diagram shows the wireless communication mechanisms 708, the stimulation mechanisms 712 and the physiological sensor mechanisms 714 described previously and other devices that are not visible in the previous figures such as the processor 700, volatile memory 702, non-volatile memory 704, and wired communication mechanisms 710.

The patient worn module may include one or more types of memory. For example, a non-volatile memory 704, such as a flash memory, may be used to store instructions for the processor while the patient worn module is powered down. When the patient worn module is powered on, these instructions may be copied to a faster, volatile memory 702, such as synchronous dynamic random access memory (SDRAM) by a basic input/output system (BIOS) or the like. Once the volatile memory 702 is loaded with instructions, the processor 700 executes the instructions stored in the volatile memory 702. These instructions control the operation of the processor 700; that is, the processor 700 is programmed by these instructions to perform the operations described herein.

The non-volatile memory 704 may also store data while the patient worn module is powered down, so if the battery becomes exhausted, this data will be available after the battery is recharged or replaced. The processor 700 may optionally store configuration settings for the controls that determine the characteristics of the repeating pattern of stimulation in the non-volatile memory 704.

The patient worn modules may include one or more wired communication mechanisms 710, which may be coupled to a wired communication port 706. The wired communication port 706 may be coupled to external computer systems using suitable wired communication devices. The processor 700 may communicate with external computer systems and may exchange data with those systems. The processor 700 may optionally transmit data stored in non-volatile memory 704, or volatile memory 702 to external computer systems for purposes of analysis. The processor 700 may also optionally receive data from external computer systems and store this data in non-volatile memory 704 or volatile memory 702. For example, said data may be used to change the default configuration characteristics of the repeating pattern of stimulation. The processor 700 may also optionally receive instructions from external computer systems that it stores in non-volatile memory 704 which may be used to control the operation of the processor 700 as described previously.

Although not shown in FIG. 7, the patient worn modules may include a bus to interconnect the processor 700 and the wireless communication mechanisms 708, the non-volatile memory 704, the volatile memory 702, the wired communication mechanisms 710, the stimulation mechanisms 712 and the physiological sensor mechanisms 714. The patient worn modules 110 may also include other circuits (not shown) to automatically connect the battery, processor 700 and other components.

The patient worn modules may include zero or more stimulation mechanisms 712, which may be coupled to the processor 700 and which respond to instructions received from the processor 700 to create control signals that determine the activation characteristics of the stimulators previously described, which provide the previously described repeating pattern of stimulation. The stimulation mechanisms 712 may comprise suitable electronic devices that provide stimulations when coupled to a patient. The stimulation mechanism may optionally comprise a vibration motor, which may include an eccentric mass counter weight attached to the shaft of a motor, which when activated, causes a tactile stimulation when coupled to a patient. The stimulation mechanism may also optionally comprise a vibration motor, which may include a mass attached to the shaft of a linear motor, which when activated, causes a tactile stimulation when coupled to a patient. The stimulation mechanism may also optionally comprise a piezoelectric vibration motor, which when activated, causes a tactile stimulation when coupled to a patient. The stimulation mechanism may also optionally comprise an electroactive polymer, which responds to an induced electrical current by contracting, causing a tactile stimulation when coupled to a patient. The stimulation mechanism may also optionally comprise transcutaneous electrical nerve stimulators (TENS), which stimulate nerves through the induction of an electrical current when coupled to a patient. The stimulation mechanism may also optionally comprise multiple light emitting diodes (LEDs) that, when activated cause a visual stimulation when coupled to a patient. The stimulation mechanism may also optionally comprise multiple acoustic audio transducers that, when activated cause an audible stimulation when coupled to a patient. The stimulation mechanism may also optionally comprise any combination of vibration motor, electroactive polymer, TENS, LEDs, acoustic audio transducers, or other suitable devices.

The patient worn modules may include zero or more physiological sensor mechanisms 714, which may be coupled to the processor 700 and which transmit data to the processor indicative of the physiological state of a patient. The processor 700 may optionally process this physiological data and consequently modify the characteristics of the repeating pattern of stimulation as described previously. The processor 700 may optionally transmit the physiological data to the controller 100 as described previously. The physiological sensor mechanism may optionally comprise one or more actimetry sensors, which detect gross motor movement when coupled to a patient. The physiological sensor mechanism may also optionally comprise one or more Electroencephalography (EEG) sensors, which detect electrical activity of the brain when coupled to a patient. The physiological sensor mechanism may also optionally comprise one or more respiratory sensors, which detect the respiration rate when coupled to a patient. The physiological sensor mechanism may also optionally comprise one or more heart rate sensors, which detect the heart rate when coupled to a patient. The physiological sensor mechanism may also optionally comprise one or more body temperature sensors, which detect body temperature when coupled to a patient. The physiological sensor mechanism may also optionally comprise one or more blood pressure sensors, which detect blood pressure when coupled to a patient. The physiological sensor mechanisms may also optionally comprise any combination of actimetry sensors, EEG sensors, respiratory sensors, heart rate sensors, body temperature sensors, blood pressure sensors or other physiological sensor.

FIG. 8 Description

Figure 8:
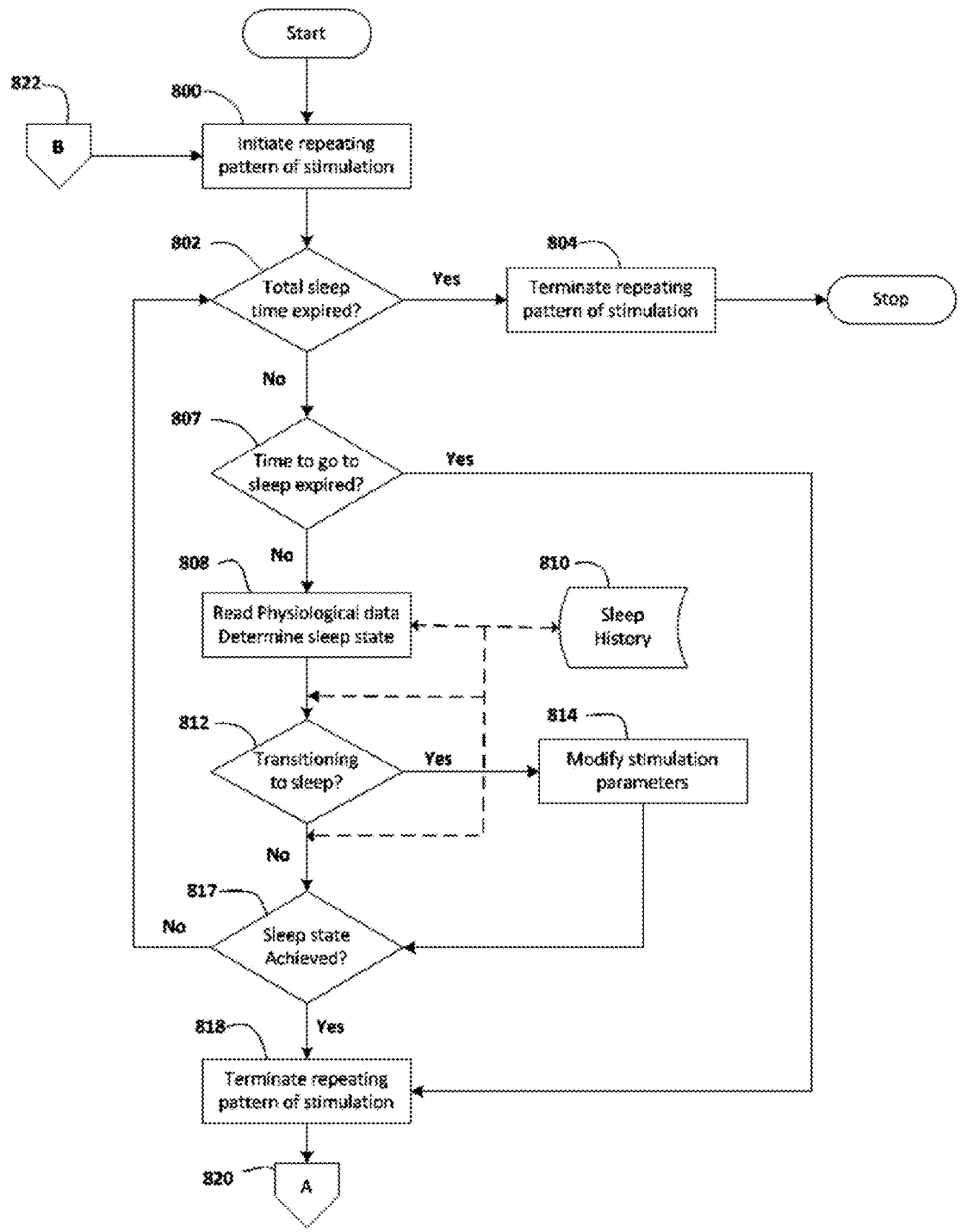
FIG. 8 is a flowchart that illustrates operations performed, according to one embodiment of the present invention wherein the device is initiating and/or accelerating the onset of sleep.

FIG. 8 is a flowchart that illustrates operation of one embodiment of the present invention. At 800 execution of the previously described repeating pattern of stimulation is initiated according to preconfigured parameters which determine the characteristics of the repeating pattern of stimulation, and control passes to decision block 802. At 802 the preconfigured parameter, which determines the total time for execution of the controller 100 per sleep session, is compared to the elapsed time of execution of the controller 100 since the initiation of the first repeating pattern of stimulation of the current sleep session. If the elapsed time of execution since the initiation of the first repeating pattern of stimulation of the current sleep session exceeds the preconfigured parameter which determines the total time for execution of the controller 100 per sleep session, control is passed to 804, otherwise control passes to decision block 807. At 804 the repeating pattern of stimulation is terminated and all operations are stopped.

At decision block 807 the preconfigured parameter, which determines the total time for execution of any single repeating pattern of stimulation, is compared to the elapsed time of execution of the currently executing repeating pattern of stimulation. If the elapsed time of execution of the currently executing repeating pattern of stimulation exceeds the preconfigured parameter which determines the total time for execution of any single repeating pattern of stimulation, control is passed to 818, otherwise control passes to 808.

At 808 physiological data are acquired from one or more patient worn modules and are processed to generate data indicative of the patient's current pattern of wakefulness, and sequential physiological data, which are optionally stored in the Sleep History data store 810 as described previously in FIGS. 1, 2, 3, 4, 5, and 6, and control is passed to decision block 812.

At decision block 812 data from the Sleep History data store 810 are processed to determine if the patient is experiencing a transition to sleep as described previously in FIGS. 1, 2, 3, 4, 5, and 6. If such a transition is occurring, control passes to block 814, otherwise control passes to decision block 817. At 814 the parameters of the repeating pattern of stimulation are optionally modified as described previously, and control passes to decision block 817.

At decision block 817 data from the Sleep History data store 810 are processed to determine if the patient has achieved a sleep state. If a sleep state has been achieved, control passes to block 818, otherwise it passes to block 802 and execution continues as described above.

At 818 execution of the repeating pattern of stimulation is terminated and control passes to block 820.

FIG. 9 Description

Figure 9:
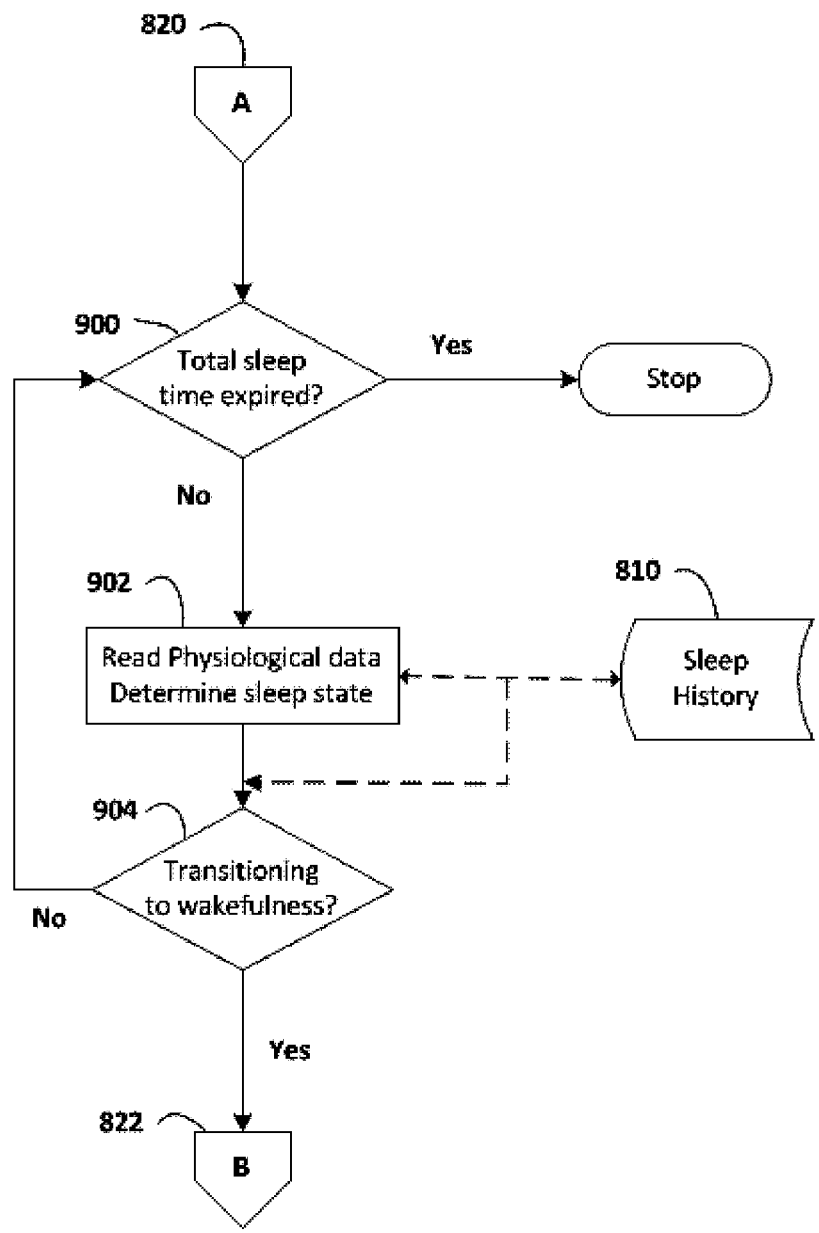
FIG. 9 is a flowchart that illustrates operations performed, according to one embodiment of the present invention, wherein the device determines if the patient is transitioning from a state of sleep to a state of wakefulness.

FIG. 9 is a continuation of the flowchart in FIG. 8. Control passes from block 820 to decision block 900. At 900 the preconfigured parameter, which determines the total time for execution of the controller 100 per sleep session, is compared to the elapsed time of execution of the controller 100 since the initiation of the first repeating pattern of stimulation of the current sleep session. If the elapsed time of execution since the initiation of the first repeating pattern of stimulation of the current sleep session exceeds the preconfigured parameter which determines the total time for execution of the controller 100 per sleep session, all operations are stopped. Otherwise controls passes to block 902.

At 902 physiological data are acquired from one or more patient worn modules and are processed to generate data indicative of the patient's current pattern of wakefulness, and sequential physiological data, which are optionally stored in the Sleep History data store 810 as described previously in FIGS. 1, 2, 3, 4, 5, and 6, and control is passed to decision block 904.

At decision block 904 data from the Sleep History data store 810 are processed to determine if the patient is experiencing a transition to wakefulness from sleep as described previously in FIGS. 1, 2, 3, 4, 5, and 6. If such a transition is occurring, control passes to block 822, otherwise control passes to decision block 900 and operations continue as described above.

At block 822, control passes to block 800 and the repeating pattern of stimulation is re-initiated as described in FIG. 8.

A medical device for initiating and/or accelerating onset of sleep and maintaining the sleep state after sleep onset, through delivery of alternate bilateral stimulation to a patient in response to physiological characteristics of the patient has been described as including processors controlled by instructions stored in a memory. The memory may be random access memory (RAM), read-only memory (ROM), flash memory or any other memory, or combination thereof, suitable for storing control software or other instructions and data. Some of the functions performed by the medical device have been described with reference to flowcharts and/or block diagrams. Those skilled in the art should readily appreciate that functions, operations, decisions, etc. of all or a portion of each block, or a combination of blocks, of the flowcharts or block diagrams may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. For example, although some aspects of the medical device have been described with reference to a flowchart, those skilled in the art should readily appreciate that functions, operations, decisions, etc. of all or a portion of each block, or a combination of blocks, of the flowchart may be combined, separated into separate operations or performed in other orders. Furthermore, disclosed aspects, or portions of these aspects, may be combined in ways not listed above. Accordingly, the invention should not be viewed as being limited to the disclosed embodiments.

By way of example, and for illustrative purposes, components of the medical device described herein may include one or more of the following:

In one embodiment of this device, the patient worn modules could be implemented with the Sony Ericsson SmartWatch, and the controller could be implemented with the Sony Ericsson Xperia mini pro smart phone.

The SmartWatch incorporates a vibration motor capable of providing tactile stimulation, an accelerometer capable of determining gross body movements, a Blue Tooth communication mechanism, memory and a processor, which is coupled to the vibration motor, the accelerometer, the memory and the Blue Tooth communication mechanism. The processor in the SmartWatch can be independently programmed using the Android open source software platform to control the operation of the vibration motor, interpret signals from the accelerometer and to communicate with other devices using Blue Tooth.

The Xperia mini pro incorporates a touch sensitive screen, a Blue Tooth communication mechanism, memory and a processor, which is coupled to the touch sensitive screen, the Blue Tooth communication mechanism and the memory. The processor in the Xperia mini pro can be independently programmed using the Android open source software platform to communicate with the SmartWatch to receive physiological data and to transmit signals that control the SmartWatch. The processor can be programmed to respond to the physiological data by transmitting control signals to the SmartWatch that modify the operation of the vibration motor. The processor in the Xperia mini pro can also be programmed to provide user accessible controls on the touch sensitive screen, and to interpret the values of these controls to control the operation of the SmartWatch.

The patient worn modules could also be constructed from commercially available components. For example, microcontrollers incorporating processors and memory are available from a number of vendors, including the AVR family from Atmel Corporation, and the Programmable System-on-Chip family from Cypress Semiconductor. Multiple wireless communication mechanisms are available that support the Blue Tooth and Zigbee wireless communication standards, such as the Atheros Radio-On-Chip for Mobile family of products from Qualcomm, and the Bluetooth 4.0 Low Energy Modules from Panasonic.

A person of ordinary skill in the art would also recognize that the patient worn modules could be constructed from commercially available physiological sensors including:

the wireless headband and EEG sensor from Zeo, the WakeMate actimetry wristband from WakeMate, the MEMS series of accelerometers from Analog Devices,
the H7 heart rate sensor from Polar,
the Acoustic Respiratory sensor from Masimo,
the AD592 integrated circuit temperature transducer from Analog Devices.

A patient may optionally use the device before attempting to initiate sleep by turning on the controller and turning on two patient worn modules, which each contain a stimulator comprising a vibration motor constructed of a small electrical motor with an eccentric mass counter weight mounted to its shaft, and, a physiological sensor comprising an actimetry sensor constructed of a three-axis accelerometer. The patient then connects the two patient worn modules to the controller through a wireless communication mechanism and attaches the patient worn modules to individual adjustable belts and secures one belt around each of the patient's wrists. The patient adjusts the user accessible controls on the controller to:

set the desired initial characteristics of the repeating pattern of stimulation, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

A patient may also optionally use the device before attempting to initiate sleep by turning on the controller, turning on two patient worn modules, which each contain a stimulator comprising a vibration motor constructed of a small linear electrical motor with a mass mounted to its shaft, and turning on a third patient worn module which contains a physiological sensor comprising a blood pressure sensor. The patient then connects the three modules to the controller through a wireless communication mechanism and attaches the two modules containing stimulators to individual adjustable belts and secures one belt around each of the patient's wrists, and attaching the third module containing a blood pressure sensor to a separate belt and secures the belt around the patient's arm such that it will detect the patient's blood pressure. The patient adjusts the user accessible controls on the controller to:

set the desired initial characteristics of the repeating pattern of stimulation, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

A patient may also optionally use the device before attempting to initiate sleep by turning on the controller, turning on two patient worn modules, which each contain a stimulator comprising transcutaneous electrical nerve stimulators (TENS), and turning on a third patient worn module which contains a physiological sensor comprising a body temperature sensor. The patient then connects the three modules to the controller through a wireless communication mechanism and attaches the two modules containing stimulators to individual adjustable belts and secures one belt around each of the patient's wrists, and attaching the third module containing the body temperature sensor to a separate belt and secures the belt around the patient's arm such that it will detect the patient's body temperature. The patient adjusts the user accessible controls on the controller to:

set the desired initial characteristics of the repeating pattern of stimulation, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

A patient may also optionally use the device before attempting to initiate sleep by turning on the controller, turning on one patient worn module, which contains a stimulator comprising multiple light emitting diodes (LEDs) arranged in a horizontal array and turns on two additional patient worn modules, which each contain a physiological sensor comprising an Electroencephalography (EEG) sensor. The LEDs are arranged in a horizontal array such that when activated, the LEDs will generate a repeating pattern of stimulation by energizing and de-energizing the LEDs sequentially from one end of the array to the other, pausing for a period of time and then energizing and de-energizing the LEDs sequentially in the reverse order, and then pausing for a period of time before repeating the entire sequence. The patient connects the three modules to the controller through a wireless communication mechanism and attaches the three modules to a single adjustable belt, securing said belt around the patient's head such that the modules containing the LEDs are positioned over the patient's eyes and centered horizontally over the patient's nose and the modules containing the EEG sensors are positioned to detect the electrical activity of the patient's brain. The patient adjusts the user accessible controls on the controller to:

set the desired initial characteristics of the repeating pattern of stimulation, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

A patient may also optionally use the device before attempting to initiate sleep by turning on the controller, turning on two patient worn modules, which each contain a stimulator comprising an acoustic audio transducer and turning on two additional patient worn modules, which each contain a physiological sensor comprising an Electroencephalography (EEG) sensor. The patient connects the four modules to the controller through a wireless communication mechanism and attaches the four modules to a single adjustable belt, secures the belt around the patient's head such that one module containing an acoustic audio transducer is positioned over each of the patient's ears, and the two modules containing the EEG sensors are positioned to detect the electrical activity of the patient's brain. The patient adjusts the user accessible controls on the controller to:

set the desired initial characteristics of the repeating pattern of stimulation, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

A patient may also optionally use the device before attempting to initiate sleep by turning on the controller, turning on two patient worn modules, which each contain a stimulator comprising an electroactive polymer material and turning on a third patient worn module, which contains a physiological sensor comprising a respiratory sensor. The patient then connects the three modules to the controller through a wireless communication mechanism and attaches the three modules to a single adjustable belt and secures the belt around the patient's torso such that the two modules containing the stimulators are positioned on opposite lateral sides of the patient's body, and the third module is positioned to detect the patient's respiration. The patient adjusts the user accessible controls on the controller to:

set the desired initial characteristics of the repeating pattern of stimulation, synchronize the periodicity of the stimulations with the periodicity of the patient's respiration rate, detect when the patient is transitioning to a sleep state and to consequently reduce the intensity of the stimulations, detect when the patient is in a stable sleep state and to consequently terminate the stimulations, detect when the patient is being aroused from sleep after initial onset of sleep, and to consequently resume the repeating pattern of stimulation, set a length of time after which the controller will terminate the stimulations, and, set a length of time after which the controller will stop attempting to initiate or maintain the sleep state of the patient.

I claim:

1. A medical device for initiating onset of sleep through controlled delivery of bilateral stimulation to a patient, the device comprising:

a first and second stimulation module configured to provide alternate bilateral stimulation to at least two bilateral positions on the patient's body such that one position is stimulated in a first time interval and a second position is stimulated in a second time interval, wherein the stimulation comprises any of a tactile, an auditory and an electrical stimulation;

one or more physiological sensors configured to be positioned on the patient to provide feedback for modifying the bilateral stimulation to the patient; and a controller, which is in communication with the stimulation modules and the one or more physiological sensors, to optimize bilateral stimulation to the patient for initiation of the onset of sleep in response to the physiological feedback from the one or more physiological sensors;

wherein the feedback from the physiological sensors together with the modification to the stimulation modules maintains a state of sleep in the patient after the onset of sleep; and wherein the alternate bilateral stimulation is separated by a period of time when neither stimulation module is activated.

2. The medical device of claim 1, wherein an intensity of the stimulation is controlled in response to the physiological feedback from the one or more physiological sensors.

3. The medical device of claim 1, wherein a duration of the first time interval and the second time interval is controlled in response to the physiological feedback from the one or more physiological sensors.

4. The medical device of claim 1, wherein the period of time when neither stimulation module is activated is controlled in response to the physiological feedback from the one or more physiological sensors.

5. The medical device of claim 1, wherein the first and second stimulation modules comprise one or more vibration motors.

6. The medical device of claim 5, wherein the one or more vibration motors incorporate an eccentric mass counter weight attached to a shaft of a rotating motor.

7. The medical device of claim 5, wherein the one or more vibration motors incorporate a mass attached to a shaft of a linear motor.

8. The medical device of claim 5, wherein the one or more vibration motors incorporate a piezoelectric motor.

9. The medical device of claim 1, wherein the first and second stimulation modules comprise one or more electroactive polymers.

10. The medical device of claim 1, wherein the first and second stimulation modules comprise one or more transcutaneous electrical nerve stimulators.

11. The medical device of claim 1, wherein the first and second stimulation modules comprise one or more acoustic audio transducers.

12. The medical device of claim 1, wherein the one or more physiological sensors comprise actimetry sensors.

13. The medical device of claim 1, wherein the one or more physiological sensors comprise electroencephalography sensors.

14. The medical device of claim 1, wherein the one or more physiological sensors comprise respiratory sensors.

15. The medical device of claim 1, wherein the one or more physiological sensors comprise heart rate sensors.

16. The medical device of claim 1, wherein the one or more physiological sensors comprise body temperature sensors.

17. The medical device of claim 1, wherein the one or more physiological sensors comprise blood pressure sensors.

18. A method for initiating onset of sleep through controlled delivery of alternate bilateral stimulation to a patient, comprising:

placing a first and second stimulation module configured to provide alternate bilateral stimulation to at least two bilateral positions on the patient's body, wherein the stimulation comprises any of a tactile, an auditory and an electrical stimulation;

placing one or more physiological sensors positioned on the patient to provide feedback for modifying the alternate bilateral stimulation to the patient;

activating the first and the second stimulation module such that one bilateral position is stimulated in a first time interval and a second bilateral position is stimulated in a second time interval;

controlling the alternate bilateral stimulation provided by the stimulation modules in response to feedback from the one or more physiological sensors to optimize the bilateral stimulation to the patient for initiation of the onset of sleep; and
maintaining a sleep state after the onset of sleep.

19. A method according to claim 18, wherein the alternate bilateral stimulation is separated by a period of time when no position on the patient's body is stimulated.

20. A method according to claim 19, further comprising:
measuring the patient's state of wakefulness, and automatically modifying the alternate bilateral stimulation in response to a change of the patient's measured state of wakefulness.

21. A method according to claim 20, wherein:
the patient's state of wakefulness is derived from the electrical activity of the patient's brain.

22. A method according to claim 20, wherein:
the patient's state of wakefulness is derived from the patient's gross motor movements.

23. A method according to claim 20, wherein:
the patient's state of wakefulness is derived from the patient's respiration rate.

24. A method according to claim 20, wherein:
the patient's state of wakefulness is derived from the patient's heart rate.

25. A method according to claim 20, wherein:
the patient's state of wakefulness is derived from the patient's body temperature.

26. A method according to claim 20, wherein:
the patient's state of wakefulness is derived from the patient's blood pressure.

27. A method according to claim 20, further comprising:
ascertaining the patient's state of wakefulness through a comparison of current and recent physiological conditions of the patient to previously obtained standard data.

28. A method according to claim 20, further comprising:
ascertaining the patient's state of wakefulness through a comparison of current and recent physiological conditions of the patient to previously obtained historical values of the patient.

29. A method according to claim 20, further comprising:
ascertaining changes to the patient's state of wakefulness through a comparison of current and recent states of wakefulness of the patient to previously obtained standard data.

30. A method according to claim 20, further comprising:
ascertaining changes to the patient's state of wakefulness through a comparison of current and recent states of wakefulness of the patient to previously obtained historical values of the patient.

31. A method according to claim 20, further comprising:
obtaining physiological feedback indicative of the patient's state of wakefulness from said one or more physiological sensors, and automatically reducing an intensity of stimulations to the at least two bilateral positions on the patient's body.

32. A method according to claim 20, further comprising:
obtaining physiological feedback indicative of the patient's state of wakefulness from said one or more physiological sensors, and automatically terminating stimulations to the at least two bilateral positions on the patient's body.

33. A method according to claim 20, further comprising:
obtaining physiological feedback indicative of the patient's state of wakefulness from said one or more physiological sensors, and automatically initiating stimulations to the at least two bilateral positions on the patient's body.

34. A method according to claim 20, further comprising:
obtaining physiological feedback indicative of the patient's state of wakefulness from said one or more physiological sensors, and automatically increasing an intensity of stimulations to the at least two bilateral positions on the patient's body.

35. A method according to claim 19, further comprising:
obtaining the patient's respiration rate, and automatically controlling the alternate bilateral stimulation.

36. A method according to claim 35, wherein the patient's respiration rate is greater than a defined non-zero respiration rate.

37. A method according to claim 36, further comprising:
determining a difference between the patient's respiration rate and the defined respiration rate, and automatically controlling the alternate bilateral stimulation.

38. A method according to claim 37, wherein:
the defined respiration rate is determined from previously obtained standard data.

39. A method according to claim 37, wherein:
the defined respiration rate is determined from obtained historical values of the patient's sleep respiration rate.

40. A method according to claim 37, further comprising:
in response to the difference between the patient's respiration rate and the defined respiration rate being greater than a percentage of the defined rate, configurable between 20% and 200%, modifying a duration of at least one of said first time interval, said second time interval and said period of time when no position on the patient's body is stimulated.

41. A method according to claim 40, wherein the sum of the duration of time for said first time interval, said second time interval and said period of time when no position on the patient's body is stimulated is equal to the defined rate plus a percentage of the difference between the patient's respiration rate and the defined rate, configurable between 20% and 80%.

42. A method according to claim 41, wherein the duration of time for said first time interval, said second time interval and said period of time when no position on the patient's body is stimulated is configurable to between 10% and 70% of the total sum of time, the total sum of the percentages of time is equal to 100%.

* * * * *